US008598383B2

(12) United States Patent
Gwag et al.

(10) Patent No.: US 8,598,383 B2
(45) Date of Patent: Dec. 3, 2013

(54) PHARMACEUTICAL COMPOSITION FOR TREATING OR PREVENTING DEGENERATIVE AND INFLAMMATORY DISEASES

(75) Inventors: Byoung-Joo Gwag, Suwon-si (KR); Sung-Ig Cho, Seoul (KR); Jae-Young Cho, Suwon-si (KR); Young-Ae Lee, Suwon-si (KR); Han-Yeol Byun, Seongnam-si (KR); Doo-Soon Lim, Seoul (KR); Ki-Baik Hahm, Suwon-si (KR); Young-Bae Kwon, Jeonju-si (KR); Jin-Hwan Lee, Seongnam-si (KR); Bok-Seon Yoon, Suwon-si (KR); Chun-San An, Suwon-si (KR); Keun-Sil Ryu, Suwon-si (KR)

(73) Assignee: Neurotech Pharmaceuticals Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/453,978

(22) Filed: Apr. 23, 2012

(65) Prior Publication Data

US 2012/0209025 A1    Aug. 16, 2012

Related U.S. Application Data

(60) Division of application No. 12/421,442, filed on Apr. 9, 2009, now abandoned, which is a continuation of application No. 12/296,747, filed as application No. PCT/KR2007/001801 on Apr. 13, 2007, now Pat. No. 8,455,470.

(30) Foreign Application Priority Data

Apr. 13, 2006 (KR) .......................... 10-2006-0033596

(51) Int. Cl.
*C07C 51/00* (2006.01)
(52) U.S. Cl.
USPC ........................................................ 562/515
(58) Field of Classification Search
USPC ........................................................ 562/515
See application file for complete search history.

(56) References Cited

U.S. PATENT DOCUMENTS

| 3,632,760 | A | 1/1972 | Shen et al. |
| 3,674,844 | A | 7/1972 | Shen et al. |
| 6,573,402 | B1 | 6/2003 | Gwag et al. |
| 6,927,303 | B2 | 8/2005 | Gwag et al. |
| 6,964,982 | B2 | 11/2005 | Gwag et al. |
| 7,189,878 | B2 | 3/2007 | Gwag et al. |
| 7,319,160 | B2 | 1/2008 | Gwag et al. |
| 7,371,896 | B2 | 5/2008 | Gwag et al. |
| 2002/0010335 | A1* | 1/2002 | Chiu et al. ................... 544/350 |
| 2002/0137791 | A1* | 9/2002 | Honda et al. ................. 514/459 |
| 2006/0128677 | A1 | 6/2006 | Gwag et al. |
| 2007/0049565 | A1 | 3/2007 | Gwag et al. |
| 2007/0298129 | A1 | 12/2007 | Gwag et al. |

FOREIGN PATENT DOCUMENTS

| DE | 2031227 | 1/1971 |
| EP | 0122827 A1 | 10/1984 |
| JP | 54-125632 | 9/1979 |
| JP | 60-237041 | 11/1985 |
| WO | WO 86/03199 | 6/1986 |
| WO | WO 94/13663 | 6/1994 |
| WO | WO 01/79153 A1 | 10/2001 |

OTHER PUBLICATIONS

Andersen et al, "Do Nonsteroidal Anti-Inflammatory Drugs Decrease the Risk for Alzheimer's Disease?," Neurology, (vol. 45), (p. 1441-1445), (Aug. 1995).
Grisham et al, "Prooxidant Properties of 5-Aminosalicylic Acid Possible Mechanism for its Adverse Side Effects," Digestive Diseases and Sciences, Plenum Publishing Corporation, (vol. 37), (Issue 9), (p. 1383-1389), (Sep. 1992).
Singh et al, "Effect of 5-Lipoxygenase Inhibition on Events Associated with Inflammatory Bowel Disease in Rats," Indian Journal of Experimental Biology, (vol. 42), (p. 667-673), (Jul. 2004).
Singh et al, "Effect of Nimesulide on Acetic Acid- and Leukotriene-Induced Inflammatory Bowel Disease in Rats," Prostaglandins & other Lipid Mediators, Elsevier Science Inc., (vol. 71), (p. 163-175), (2003).
Song et al, "Inhibition of Cyclooxygenase-2 Ameliorates the Severity of Pancreatitis and Associated Lung Injury," Am J Physiol Gastrointestinal and Liver Physiology, American Physiological Society, (vol. 283), (p. 1166-1174), (Jul. 17, 2002).
Deans and Sattar, "'Anti-Inflammatory" Drugs and Their Effects on Type 2 Diabetes," Diabetes Technology & Therapeutics, (vol. 8), (Issue 1), (p. 18-27), (2006).
Yang et al, "The Novel Anti-inflammatory Compound, Lisofylline, Prevents Diabetes in Multiple Low-Dose Streptozotocin-Treated Mice," Pancreas, Lippincott Williams & Wilkins, (vol. 26), (Issue. 4), (p. e99-e104), (2003).
Burleigh et al, "Cyclooxygenase-2 Promotes Early Atherosclerotic Lesion Formation in ApoE-Deficient and C57BL/6 Mice," Journal of Molecular and Cellular Cardiology, Elsevier, (vol. 39), (p. 443-452), (2005).
West et al, "The Arachidonic Acid 5-Lipoxygenase Inhibotor Nordihydroguaiaretic Acid Inhibits Tumor Necrosis Factor Alpha Activation of Microglia and Extends Survival of G93A-SOD1 Transgenic Mice," Journal of Neurochemistry, International Society for Neurochemistry, (vol. 91). (p. 133-143), (2004).

(Continued)

Primary Examiner — Brandon Fetterolf
Assistant Examiner — Christopher R Stone
(74) Attorney, Agent, or Firm — Yancy IP Law, PLLC

(57) ABSTRACT

The present invention relates to a pharmaceutical composition useful for treating or preventing inflammatory disease and cell damage, and a method for treating or preventing inflammatory disease and cell damage. The present invention uses the 2-hydroxybenzoic acid derivative represented by the specific chemical formula or its pharmaceutically acceptable salt. The compound of the present invention is useful for treating or preventing cell damage and inflammatory disease including gastritis, gastric ulcer, pancreatitis, colitis, arthritis, diabetes, arteriosclerosis, nephritis, hepatitis, Alzheimer's disease, Parkinson's disease and Lou Gehrig's disease.

1 Claim, 17 Drawing Sheets

(56) References Cited

OTHER PUBLICATIONS

Mysek et al, "Chloromethylation of 4-Arenesulfonyl-N-Methyl-Amidoanisoles," Chemical Abstracts, (vol. 67), (Issue 5), (p. 1671 & 2034), (Jul. 31, 1967).
Nussbaumer et al, "Novel Antiproliferative Agents Derived from Lavendustin A," J. Med. Chem., vol. 37 ( No. 24), p. 4079-4084, (1994).
Rizzi et al, "Electron Impact Mass Spectrometry of Some 5-Aminosalicyclic Acid Derivatives," Chemical Abstracts, American Chemical Society, vol. 120 ( No. 15), p. 972, (Apr. 11, 1994).
Spector et al, "The Effects of Salicylate and Probenecid on the Cerebrospinal Fluid Transport of Penicillin, Aminosalicylic Acid and Iodide," The Journal of Pharmacology and Experimental Therapeutics, The Williams & Wilkins Co., vol. 188 ( No. 2), p. 55-65, (1974).
Kumamoto et al, "Inhibition by Aminosalicylates of Lipid Peroxidation in Large Intestinal Mucosa after Mesenteric Ischemia/Reperfusion in the Rat," The Japanese Journal of Pharmacology, vol. 75 ( No. 2), p. 187-189, (1997).
Webster's II, New Riverside University Dictionary, The Riverside Publishing Company, p. 933, (1984).
Fischer-Nielsen et al, "8-Hydroxydeoxyguanosine in Vitro: Effects of Glutathione, Ascorbate, and 5-Aminosalicylic Acid," Free Radical Biology & Medicine, Pergamon Press Ltd., p. 121-126, (1992).
Gerlach et al, "Altered Brain Metabolism of Iron as a Cause of Neurodegenerativae Diseases?," Journal of Neurochemistry, Raven Press, Ltd., vol. 63 ( No. 3), p. 793-807, (1994).
Gilgun-Sherki et al, "Antioxidant Therapy in Acute Central Nervous System Injury: Current State," Pharmacological Reviews, The American Society for Pharmacology and Experimental Therapeutics, vol. 54 ( No. 2), p. 271-284, (2002).
Hussain et al, "Dose Loading with Delayed-Release Mesalazine: A Study of Tissue Drug Concentrations and Standard Pharmacokinetic Parameters," Br J Clin Pharmacol, Blackwell Science Ltd., vol. 49 ( No. 4), p. 323-330, (Apr. 2000).
Klotz and Stracciari, "Steady State Disposition of 5-Aminosalicyclic Acid Following Oral Dosing," Arzneimittel-Forschung, vol. 43 ( No. 12), p. 1357-1359, (1993).
Liu and Hong, "Role of Microglia in Inflammation-Mediated Neurodegenerative Diseases: Mechanisms and Strategies for Therapeutic Intervention," The Journal of Pharmacology and Experimental Therapeutics, vol. 304 (No. 1), pp. 1-7, 2003.
Orr et al, "An Inflammatory Review of Parkinson's Disease," Progress in Neurobiology, Elsevier Science Ltd., vol. 68, pp. 325-340, 2002.
Henkel et al "Presence of Dentritic Cells, MCP-1, and Activated Microglia/Macrophages in Amyotrophic Lateral Sclerosis Spinal Cord Tissue," Annals of Neurology, Wiley-Liss, Inc., vol. 55 ( No. 2), pp. 221-235, Feb. 2004.
Luisa Minghetti, "Role of Inflammation in Neurodegenerative Diseases," Current Opinion in Neurology, Lippincott Williams & Wilkins, vol. 18, pp. 315-321, 2005.
Gao et al, "Novel Anti-Inflammatory Therapy for Parkinsons' Disease," Trends in Pharmacological Sciences, Elsevier Ltd., vol. 24 ( No. 8), pp. 395-401, Aug. 2003.
Weydt and Moller, "Neuroinflammation in the Pathogenesis of Amyotrophic Lateral Sclerosis," NeuroReport, Lippincott Williams & Wilkins, vol. 16 ( No. 6), pp. 527-531, Apr. 25, 2005.
Hoozemans et al, "Neuroinflammation and Regeneration in the Early Stages of Alzheimer's Disease Pathology," Int. J. Devl Neuroscience, Elsevier Ltd., vol. 24, pp. 157-165, 2006.
Townsend and Pratico, "Novel Therapeutic Opportunities for Alzheimer's Disease: Focus on Nonsteriodal Anti-Inflammatory Drugs," The FASEB Journal, vol. 19, pp. 1592-1601, Oct. 2005.
Ferger et al, "Salicylate Protects Against MPTP-Induced Impairments in Dopaminergic Neurotransmission at the Striatal and Nigral Level in Mice," Naunyn-Schmiedeberg's Arch Pharmacol, vol. 360, pp. 256-261, 1999.
Teismann and Ferger, "Inhibition of the Cyclooxygenase Isoenzymes COX-1 and COX-2 Provide Neuroprotection in the MPTP-Mouse Model of Parkinson's Disease," pp. 168-174, (2001).
Kiaei et al, "Integrative Role of cPLA2 with COX-2 and the Effect of Non-Steriodal Anti-Flammatory Drugs in a Transgenic Mouse Model of Amyotrophic Lateral Sclerosis," Journal of Neurochemistry, vol. 93, pp. 403-411, 2005.
Breitner et al, "Inverse Association of Anti-Inflammatory Treatments and Alzheimer's Disease: Inital Results of Co-Twin Control Study," Neurology, vol. 44, pp. 227-232, Feb. 1994.
McGeer et al, "Anti-Inflammatory Drugs and Alzheimer Disease," The Lancet, vol. 335, p. 1037, (1990).
Rich et al, "Nonsteroidal Anti-Inflammatory Drugs in Alzheimer's Disease," Neurology, vol. 45, pp. 51-55, Jan. 1995.
Matthews et al, "Cellular Mucosal Defense During *Helicobacter pylori* Infection: A Review of the Role of Glutathione and the Oxidative Pentose Pathway," *Helicobacter*, Blackwell Publishing Ltd., vol. 10 (No. 4), pp. 298-306, 2005.
Shi et al, "Potential Role of Reactive Oxygen Species in Pancreatitis-Associated Multiple Organ Dysfunction," Pancreatology, vol. 5, pp. 492-500, 2005.
Tardif, "Antioxidants and Atherosclerosis: Emerging Drug Therapies," Current Atherosclerosis Reports, vol. 7, pp. 71-77, 2005.
Oz et al, "Antioxidants as Novel Therapy in a Murine Model of Colitis," Journal of Nutritional Biochemistry, Elsevier Inc., vol. 16, pp. 297-304, 2005.
Henrotin et al, "The Role of Reactive Oxygen Species in Homeostasis and Degradation of Cartilage," OsteoArthritis and Cartilage, vol. 11, pp. 747-755, 2003.
Loguercio et al, "Oxidatiave Stress in Viral and Alcoholic Hepatitis," Free Radical Biology & Medicine, Elsevier Science Inc., vol. 34 (No. 1), pp. 1-10, 2003.
Haidara et al, "Role of Oxidative Stress in Development of Cardiovascular Complications in Diabetes Mellitus," Current Vascular Pharmacology, Bentham Science Publishers Ltd., vol. 4, pp. 215-227, 2006.
Graziani et al, "Apple Polyphenol Extracts Prevent Damage to Human Gastric Epithelial Cells in Vitro and to Rat Gastric Mucosa in Vivo," Gut, vol. 54, pp. 193-200, 2005.
Ko et al, "Ca2+-Mediated Activation of c-Jun N-Terminal Kinase and Nuclear Factor kB by NMDA in Cortical Cell Cultures," Journal of Neurochemistry, Lippincott-Raven, vol. 71 (No. 4), pp. 1390-1395, 1998.
Ryu et al, "The Novel Neuroprotective Action of Sulfasalazine Through Blockade of NMDA Receptors," The Journal of Pharmacology & Experimental Therapeutics, vol. 305 (No. 1), pp. 48-56, 2003.
Tian et al, "Antioxidant Treatment Prevents Renal Damage and Dysfunction and Reduces Arterial Pressure in Salt-Sensitive Hypertenstion," Hypertension, Journal of the American Heart Association, vol. 45, pp. 934-939, 2005.

* cited by examiner 0.5% CMC   30 mg/kg   100 mg/kg   300 mg/kg   30 mg/kg   300 mg/kg   1000 mg/kg
                      Aspirin                              Compound2

10% Vehicle   Indomethacin   Ibuprofen    Celecoxib   Compound18
              50 mg/kg       200 mg/kg    1 g/kg      1 g/kg

*P < 0.05

PHARMACEUTICAL COMPOSITION FOR TREATING OR PREVENTING DEGENERATIVE AND INFLAMMATORY DISEASES

CROSS-REFERENCE TO RELATED APPLICATIONS

This is a continuation application of U.S. Ser. No. 12/296,747 filed Oct. 10, 2008, and a divisional application of U.S. Ser. No. 12/421,442 filed Apr. 9, 2009, the entirety of each application is incorporated herein by reference.

TECHNICAL FIELD

The present invention relates to a pharmaceutical composition and a method, which are useful for treating or preventing inflammation and cell damage occurring in inflammatory disease such as gastritis, gastric ulcer, pancreatitis, colitis, arthritis, diabetes, arteriosclerosis, nephritis, hepatitis, Alzheimer's disease, Parkinson's disease and Lou Gehrig's disease.

BACKGROUND ART

Inflammation is reactions of blood membrane and cell against injury factor originated from injured cell and foreign material entered into body. 1) Metabolites of arachidonic acid, that is, prostaglandin, leukotriene, and lipoxins, 2) platelet activation factor, 3) cytokines like tumor necrosis factor-alpha, interleukin-1 (IL-1), etc. and chemokines like monocyte chemo-attractant protein (MCP-1), macrophage inflammatory protein-1alpha (MCP-1alpha), etc., 4) nitric oxide (NO), 5) reactive oxygen, 6) vasodilating factors such as histamine, serotonin, etc. are known to be materials intervening inflammation reaction. Main purpose of inflammation reaction is to remove extraneous material and injured cell (or cell tissue), but inflammation reaction can be a cause of chronic diseases like rheumarthritis and arteriosclerosis.

In case that the degree of inflammatory damage is small, limited and temporary, injury factors are removed and tissue comes back to normal state according to the termination of inflammation reaction. Inflammation reaction happening where there is large damage or regeneration ability is weak is accompanied with major tissue damage, which may cause dysfunction. Chronic inflammation reaction happening for a long time may be a cause of fatal tissue damage in rheumarthritis, arteriosclerosis, tuberculosis, chronic pulmonary disease, etc. (Pathological Basis of Disease, pp 47-86, 7th edition).

In addition, there are many literatures disclosing that inflammation plays a critical role in pathophysiology of degenerative brain disease. Microglia present in brain is activated at site where neuronal damage happens in Alzheimer's disease, Parkinson's disease and Lou Gehrig's disease (Liu B and Hong J S. J Pharmacol Exp Ther. 2003; 304(1):1-7; Orr C F et al., Prog Neurobiol. 2002; 68(5):325-40; and Henkel J S et al., Ann Neurol. 2004; 55(2):221-35). Activated microglia produces prostaglandins, cytokines, chemokines, reactive oxygen species, NO, etc., which begin inflammation reaction in brain (Minghetti L. Curr Opin Neurol. 2005; 18(3):315-21; Gao H M, Trends Pharmacol Sci. 2003; 24(8):395-401; Weydt P and Moller T. Neuroreport. 2005; 16(6):527-31; J. J. M. Hoozemans Int. J. Devl Neuroscience. 2006; 24:157-165). Therefore, administration of drug inhibiting inflammation is reported to suppress production of beta-amyloid and plague in animal model of Alzheimer's disease (Townsend K P and Pratico D. FASEB J. 2005; 18:315-21), protect dopaminergic neuronal cell in animal model of Parkinson's disease (Ferger B et al., Naunyn Schmiedebergs Arch Pharmacol. 1999; 360(3):256-61; Teismann P, Ferger B. Synapse. 2001; 39(2):167-74), prevent death of spinal motoneuron and reduce activity of glia in Lou Gehrig's disease model (Kiaei M et al., J. Neurochem. 2005; 93(2):403-11). Actually, an attack rate of Alzheimer's disease is high in patient having brain inflammation reaction caused by contusion, etc. (Breitner J C. Neurology. 1994; 44(2):227-32), and an attack rate of Alzheimer's disease is low in rheumarthritis patient taking nonsteroidal anti-inflammatory drugs (NSAIDs) for a long time (McGeer P L et al., Lancet. 1990; 335(8696):1037). In addition, it is reported that administration of NSAID not only prevents Alzheimer's disease, but also delays progress of damage of cognitive function (Rich et al., Neurology. 1995). These results suggest that a drug inhibiting inflammation reaction may be used for preventing and treating degenerative brain disease.

NSAIDs, drugs suppressing activity of cyclooxygenase taking part in production of prostaglandin, have been developed and widely used to alleviate symptoms, including pain, of inflammatory diseases, but there are side effects to block the use of the NSAIDs. Specifically, gastrointestinal disorders such as dyspepsia, gastritis, ulcer, bleeding and perforation are side effects often happening after administration of NSAIDs. Actually, because of adverse effects of NSAIDs, 107,000 of people are reported to be hospitalized and 16,500 of people are reported to be dead in USA only. Celecoxib and Rofecoxib, selective COX-2 (cyclooxygenase-2) enzyme inhibitors, having low side effects on gastrointestinal damage have been developed and used for treating arthritis and pain. However, U.S. FDA reported that long-term administration of celecoxib, rofecoxib and valdecoxib might cause heart disease, and prohibited the use of these as drug for treating arthritis. Furthermore, clinical trials to evaluate therapeutic efficacy of celecoxib and rofecoxib in dementia were discontinued because of their safety.

In addition, reactive oxygen species produced by neutrophil, macrophage, monocyte, etc. in inflammatory disease is known to be a major reason causing tissue damage by mediating inflammatory reaction. In actually, administration of drugs removing reactive oxygen are reported to be effective in treating gastric damage happing in inflammatory diseases (Matthews G M et al., *Helicobacter.* 2005; 10(4):298-306), pancreatic damage (Shi C et al., *Pancreatology.* 2005; 5(4-5):492-500), atherosclerosis (Tardif J C. *Curr Atheroscler Rep.* 2005; 7(1):71-7), colon damage (Oz H S et al., *J Nutr Biochem.* 2005; 16(5):297-304), joint damage (Henrotin Y E et al., *Osteoarthritis Cartilage.* 2003; 11(10):747-55), renal damage (Tian N et al., *Hypertension.* 2005; 45(5):934-9), river damage (Loguercio C et al., *Free Radic Biol Med.* 2003; 34(1):1-10) and cardiovascular damage (Haidara M A et al., *Curr Vasc Pharmacol.* 2006; 4(3):215-27). Furthermore, administration of NSAIDs causes production of reactive oxygen, and induces damage to the gastric mucous membrane. This gastric damage is reported to be lessened by administration of anti-oxidant material (Graziani G et al., *Gut.* 2005; 54(2):193-200).

Inflammation plays an important role in pathophysiology of digestive disease, respiratory disease or neuronal system disease, but the use of currently available drugs is limited because of the side effects of the drugs. Aspirin (acetylsalicylic acid), an anti-inflammatory drug, is known to suppress the action of NF-kB and c-Jun N-terminal kinase (Ko H W et al., J Neurochem. 1998; 71(4):1390-5), and sulfasalazine is known to protect cell by its anti-oxidant activity (Ryu B R et al., J Pharmacol Exp Ther. 2003; 305(1):48-56). However, there is a drawback that aspirin and sulfasalazine show their cell-protecting effects in high concentration only.

DISCLOSURE

Technical Problem

Accordingly, the object of the present invention is to provide a pharmaceutical composition useful for treating or preventing inflammatory disease and having no side effects such as gastric damage and cardiovascular disorder, a treating or preventing use of the composition against inflammatory disease, and a method for treating or preventing inflammatory disease, comprising administering the composition

Technical Solution

To achieve the object, the present invention provides a pharmaceutical composition for treating or preventing inflammatory disease, comprising 2-hydroxybenzoic acid derivative represented by the below chemical formula 1 or its pharmaceutically acceptable salt as effective agent:

[Chemical formula 1]

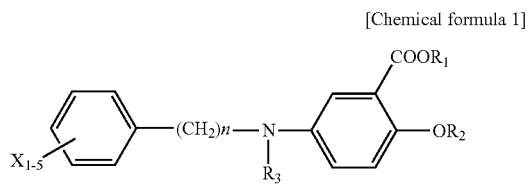

wherein,
n is an integer from 2 to 5;
$R_1$ is hydrogen or alkyl;
$R_2$ is hydrogen, alkyl or alkanoyl;
$R_3$ is hydrogen or acetoxy; and
X is independently hydrogen, nitro, halogen, alkyl, haloalkyl, alkoxy or haloalkoxy.

More preferably, the present invention provides the pharmaceutical composition, wherein the inflammatory disease is any one selected from the group consisting of gastritis, colitis, arthritis, diabetic inflammation, arteriosclerosis, nephritis, hepatitis, Alzheimer's dementia, Parkinson's disease and Lou Gehrig's disease.

The present invention also provides a method for treating or preventing inflammatory disease, comprising administering to a patient or animal suffering from inflammatory disease a therapeutically effective amount of 2-hydroxybenzoic acid derivative represented by the chemical formula 1 or its pharmaceutically acceptable salt.

The present inventors have prepared and evaluated a lot of compounds, and succeeded in inventing the fact that the 2-hydroxybenzoic acid derivative or its pharmaceutically acceptable salt is much useful for treating or preventing inflammatory disease as well as safe.

Hereinafter, the pharmaceutical composition for treating or preventing inflammatory disease and the method for treating or preventing inflammatory disease will be described in more detail.

The present invention provides a new use, that is, a use for treating or preventing inflammatory disease, of the 2-hydroxybenzoic acid derivative represented by the chemical formula 1 or its pharmaceutically acceptable salt, and also provides a method for treating or preventing inflammatory disease, using the 2-hydroxybenzoic acid derivative or its pharmaceutically acceptable salt.

[Chemical formula 1]

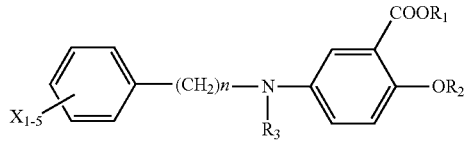

wherein,
n is an integer from 2 to 5;
$R_1$ is hydrogen or alkyl;
$R_2$ is hydrogen, alkyl or alkanoyl;
$R_3$ is hydrogen or acetoxy; and
X is independently hydrogen, nitro, halogen, alkyl, haloalkyl, alkoxy or haloalkoxy.

Preferably, in the chemical formula 1, alkyl (including 'alkyl' of haloalkyl) is $C_1$-$C_5$ alkyl, and more preferably $C_1$-$C_3$ alkyl. More specifically, preferable alkyl includes, but is not limited to, methyl, ethyl, propyl, isopropyl, butyl, sec-butyl and tert-butyl. Alkoxy (including 'alkoxy' of haloalkoxy), preferably, is $C_1$-$C_5$ alkoxy, and more preferably $C_1$-$C_3$ alkoxy. More specifically, preferable alkoxy includes, but is not limited to, methoxy, ethoxy, and propanoxy. Halogen includes, but is not limited to, fluoride, chloride, bromide, and iodide. Preferably, alkanoyl is $C_2$-$C_{10}$ alkanoyl, and more preferably $C_3$-$C_5$ alkanoyl. More specifically, preferable alkanoyl includes, but is not limited to, ethanoyl, propanoyl, and cyclohexanecarbonyl.

Preferable examples of the 2-hydroxybenzoic acid derivative include, but are not limited to, 2-hydroxy-5-phenethylamino-benzoic acid (compound 1), 2-hydroxy-5-[2-(4-trifluoromethyl-phenyl)-ethylamino]-benzoic acid (compound 2), 2-hydroxy-5-[2-(3-trifluoromethyl-phenyl)-ethylamino]-benzoic acid (compound 3), 5-[2-(3,5-bis-trifluoromethyl-phenyl)-ethylamino]-2-hydroxy-benzoic acid (compound 4), 2-hydroxy-5-[2-(2-nitro-phenyl)-ethylamino]-benzoic acid (compound 5), 5-[2-(4-chloro-phenyl)-ethylamino]-2-hydroxy-benzoic acid (compound 6), 5-[2-(3,4-difluoro-phenyl)-ethylamino]-2-hydroxy-benzoic acid (compound 7), 5-[2-(3,4-dichloro-phenyl)-ethylamino]-2-hydroxy-benzoic acid (compound 8), 5-[2-(4-fluoro-2-trifluoromethyl-phenyl)-ethylamino]-2-hydroxy-benzoic acid (compound 9), 5-[2-(2-fluoro-4-trifluoromethyl-phenyl)-ethylamino]-2-hydroxy-benzoic acid (compound 10), 2-hydroxy-5-[2-(4-methoxy-phenyl)-ethylamino]-benzoic acid (compound 11), 2-hydroxy-5-(2-o-tolyl-ethylamino)-benzoic acid (compound 12), 2-hydroxy-5-(3-phenyl-propylamino)-benzoic acid (compound 13), 2-hydroxy-5-[3-(4-trifluoromethyl-phenyl)-propylamino]-benzoic acid (compound 14), 5-[3-(4-fluoro-phenyl)-propylamino]-2-hydroxy-benzoic acid (compound 15), 5-[3-(3,4-dichloro-phenyl)-propylamino]-2-hydroxy-benzoic acid (compound 16), 2-hydroxy-5-(3-p-tolyl-propylamino)-benzoic acid (compound 17), 2-acetoxy-5-[2-(4-trifluoromethyl-phenyl)-ethylamino]-benzoic acid (compound 18), and 5-[2-(2-chloro-phenyl)-ethylamino]-2-hydroxy-benzoic acid (compound 19).

Among the preferable compounds above, 2-hydroxy-5-[2-(4-trifluoromethyl-phenyl)-ethylamino]-benzoic acid (compound 2) and 2-acetoxy-5-[2-(4-trifluoromethyl-phenyl)- ethylamino]-benzoic acid (compound 18) are more preferable as therapeutic agent for treating inflammatory disease than other 2-hydroxybenzoic acid derivatives.

Particularly, the compound 2 is more preferable than other 2-hydroxybenzoic acid derivatives when used for treating cell damage and inflammation of degenerative brain diseases. Compound 2 showed superior anti-inflammatory effect and superior suppressing effect on production of beta-amyloid compared to some compounds having similar chemical structure. Even if there are compounds showing better effect than compound 2 when considering one test only like suppressing effect on production of NO, but the compounds are not better as therapeutic agent for treating degenerative brain diseases than compound 2 because the compounds showed relatively worse effects in the other tests (for example, some compounds showed better suppressing effects on production of NO than compound 2, but the compounds showed very weak suppressing effect on production of beta-amyloid, which is very important factor in treating degenerative brain disease). In addition, some compounds showed good therapeutic efficacy in all efficacy tests, but they showed bad safety results compared to compound 2 like the following toxicity test.

Similarly, among the preferable compounds, compound 18 is more preferable in treating inflammatory disease than other 2-hydroxybenzoic acid derivatives. Compound 18 showed very much superior effect in anti-inflammatory efficacy tests compared to compounds having similar structure, and is less preferable than compound 2 in the following toxicity test.

The 2-hydroxybenzoic acid derivative of the present invention can be prepared by, but is not limited to, the below reaction schemes. The 2-hydroxybenzoic acid derivative of the present invention can be prepared by the conventional synthesis method well known in the art to which the present pertains.

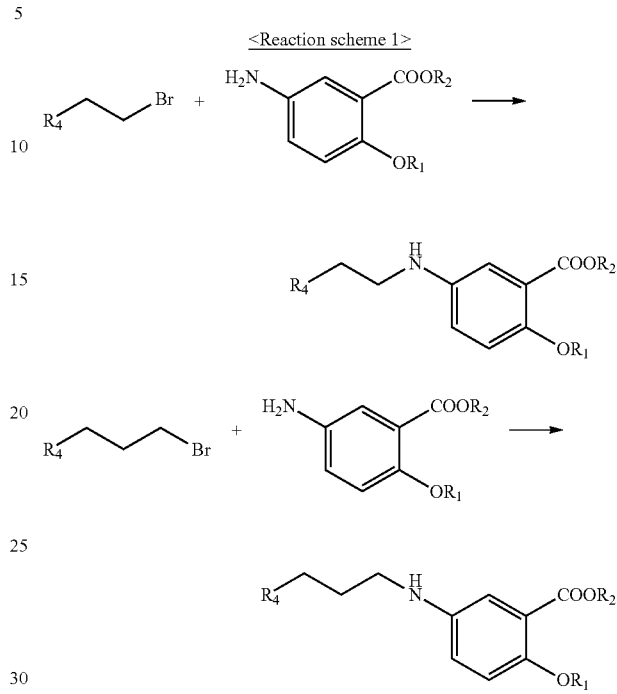

Reaction conditions: triethylamine, tetrabutylammonium iodide, N,N-dimethylformamide, room temperature, 3 hours

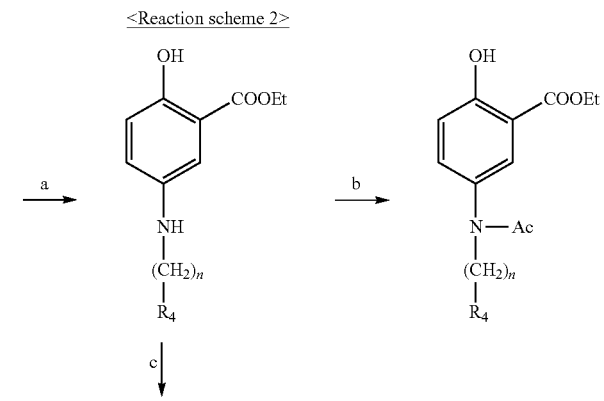

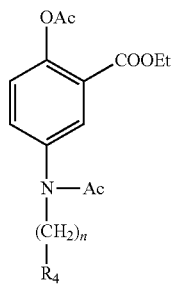

Reaction conditions: (a) ethanol, $H_2SO_4$, reflux, 6 hours; (b) acetic anhydride, methanol, 0° C., 30 minutes; (c) acetic anhydride, $H_2SO_4$, 0° C., 30 minutes In addition, 2-hydroxy-5-[2-(4-trifluoromethyl-phenyl)-ethylamino]-benzoic acid (compound 2), one preferable example of the present invention, can be prepared by, but is not limited to, the following reaction scheme 3.

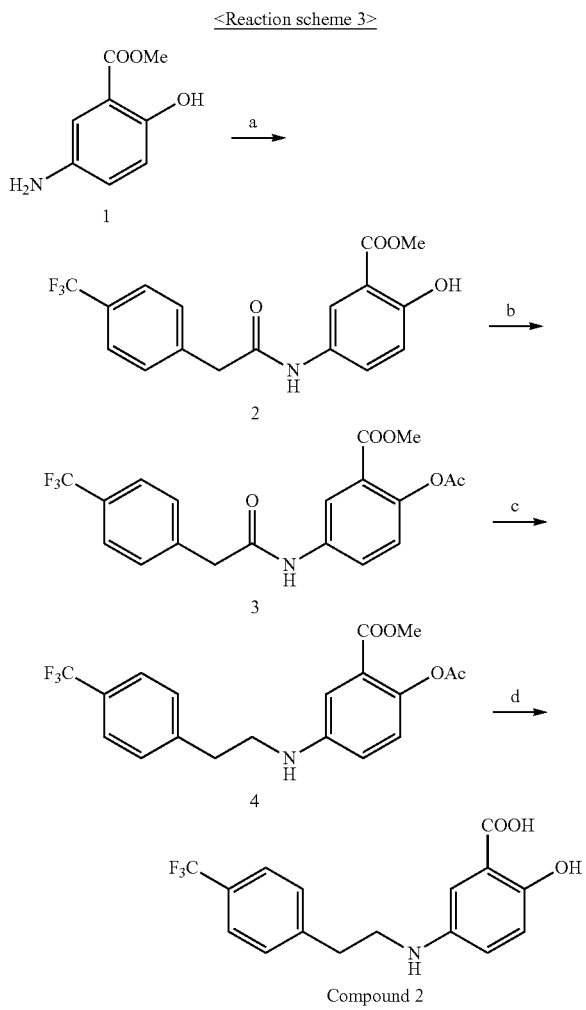

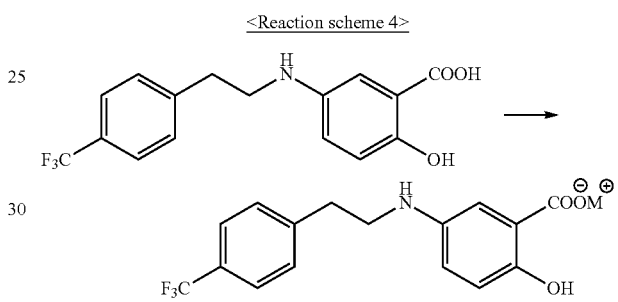

Reaction conditions: (a) 4-(trifluoromethyl)hydrocinnamic acid, $PCl_5$, xylene, reflux, 12 hours; (b) acetyl chloride, $DMF/K_2CO_3$, room temperature, 2 hours; (c) $NaBH_4$, acetic acid/1,4-dioxane, 95° C., 50 minutes; (d) $HCl/H_2O$, acetic acid The term "pharmaceutically acceptable salt" of the present invention means salts produced by non-toxic or little toxic base. In case that the compound of the present invention is acidic, base addition salts of the compound of the present invention can be made by reacting the free base of the compound with enough amount of desirable base and adequate inert solvent. Pharmaceutically acceptable base addition salt includes, but is not limited to, sodium, potassium, calcium, ammonium, magnesium or salt made by organic amino. In case that the compound of the present invention is basic, acid addition salts of the compound of the compound can be made by reacting the free base of the compound with enough amount of desirable acid and adequate inert solvent. Pharmaceutically acceptable acid addition salt includes, but is not limited to, propionic acid, isobutylic acid, oxalic acid, malic acid, malonic acid, benzoic acid, succinic acid, suberic acid, fumaric acid, mandelic acid, phthalic acid, benzenesulfonic acid, p-tolylsulfonic acid, citric acid, tartaric acid, methanesulfonic acid, hydrochloric acid, bromic acid, nitric acid, carbonic acid, monohydrogencarbonic acid, phosphoric acid, monohydrogen-phosphoric acid, dihydrogen-phosphoric acid, sulfuric acid, monohydrogen-sulfuric acid, hydrogen iodide, and phosphorous acid. In addition, the pharmaceutically acceptable salt of the present invention includes, but is not limited to, a salt of amino acid like arginate and an analog of organic acid like glucuronic or galactunoric.

For example, a pharmaceutically acceptable salt of 2-hydroxy-5-[2-(4-trifluoromethyl-phenyl)-ethylamino]-benzoic acid (compound 2), one preferable example of the present invention, can be prepared by the below reaction scheme 4. However, the following reaction methods are offered by way of illustration and are not intended to limit the scope of the invention.

In the scheme, M is a pharmaceutically acceptable metal or basic organic compound such as diethylamine, lithium, sodium and potassium.

In more detail, diethylamine salt can be prepared by dissolving a compound in alcohol, adding dropwise diethylamine, stirring the mixture, distilling in vacuo, and crystallizing the residue by adding ether. Alkali metal salt can be made by preparing desirable salt with inorganic reagent like lithium hydroxide, sodium hydroxide, potassium hydroxide in solvent like alcohol, acetone, acetonitrile and then freeze-drying. In addition, according to the similar method, lithium salt can be made with lithium acetate, sodium salt can be made with sodium 2-ethylhexanoate or sodium acetate, and potassium salt can be made with potassium acetate.

Some of the compounds of the present invention may be hydrated form, and may exist as solvated or unsolvated form. A part of compounds according to the present invention exist as crystal form or amorphous form, and any physical form is included in the scope of the present invention. In addition, some compounds of the present invention may contain one or more asymmetric carbon atoms or double bond, and therefore exists in two or more stereoisomeric forms like racemate, enantiomer, diastereomer, geometric isomer, etc. The present invention includes these individual stereoisomers of the compounds of the present invention.

The present invention also provides a pharmaceutical composition comprising the 2-hydroxybenzoic acid derivative represented by the above chemical formula 1 or its pharmaceutically acceptable salt; and pharmaceutically acceptable excipient or additive. The compound or its pharmaceutically acceptable salt of the present invention may be administered alone or with any convenient carrier, diluent, etc. and a formulation for administration may be single-dose unit or multiple-dose unit.

The pharmaceutical composition of the present invention may be formulated in a solid or liquid form. The solid formulation includes, but is not limited to, a powder, a granule, a tablet, a capsule, a suppository, etc. Also, the solid formulation may further include, but is not limited to, a diluent, a flavoring agent, a binder, a preservative, a disintegrating agent, a lubricant, a filler, etc. The liquid formulation includes, but is not limited to, a solution such as water solution and propylene glycol solution, a suspension, an emulsion, etc., and may be prepared by adding suitable additives such as a coloring agent, a flavoring agent, a stabilizer, a thickener, etc.

For example, a powder can be made by simply mixing the 2-hydroxybenzoic acid derivative of the present invention and pharmaceutically acceptable excipients like lactose, starch, microcrystalline cellulose. A granule can be prepared as follows: mixing the compound or its pharmaceutically acceptable salt, a pharmaceutically acceptable diluent and a pharmaceutically acceptable binder such as polyvinylpyrrolidone, hydroxypropylcellulose, etc; and wet-granulating with adequate solvent like water, ethanol, isopropanol, etc, or direct-compressing with compressing power. In addition, a tablet can be made by mixing the granule with a pharmaceutically acceptable lubricant such as magnesium stearate, and tabletting the mixture.

The pharmaceutical composition of the present invention may be administered in forms of, but not limited to, oral formulation, injectable formulation (for example, intramuscular, intraperitoneal, intravenous, infusion, subcutaneous, implant), inhalable, intranasal, vaginal, rectal, sublingual, transdermal, topical, etc. depending on the disorders to be treated and the patient's conditions. The composition of the present invention may be formulated in a suitable dosage unit comprising a pharmaceutically acceptable and non-toxic carrier, additive and/or vehicle, which all are generally used in the art, depending on the routes to be administered. Depot type of formulation being able to continuously release drug for desirable time also is included in the scope of the present invention.

The present invention also provides a use of the 2-hydroxybenzoic acid derivative or its pharmaceutically acceptable salt for treating and/or preventing inflammatory disease. That is, the present invention provides a pharmaceutical composition for treating or preventing inflammatory disease, comprising the 2-hydroxybenzoic acid derivative represented by the above chemical formula 1 or its pharmaceutically acceptable salt. More specifically, the 2-hydroxybenzoic acid derivative or its pharmaceutically acceptable salt can be used for treating or preventing inflammatory disease such as gastritis, gastric ulcer, pancreatitis, colitis, arthritis, diabetes, arteriosclerosis, nephritis and hepatitis, and cell damage and inflammation occurring in degenerative brain disease such as Alzheimer's dementia, Parkinson's disease and Lou Gehrig's disease. However, the use of the 2-hydroxybenzoic acid derivative or its pharmaceutically acceptable salt according to the present invention is not limited to the above concrete disease names.

For treating inflammatory disease, the compound of the present invention may be administered daily at a dose of approximately 0.01 mg/kg to approximately 100 g/kg, preferably approximately 0.1 mg/kg to approximately 10 g/kg. However, the dosage may be varied according to the patient's conditions (age, sex, body weight, etc.), the severity of patients in need thereof, the used effective components, diets, etc. The compound of the present invention may be administered once a day or several times a day in divided doses, if necessary.

BRIEF DESCRIPTION OF THE DRAWINGS

FIG. 14 shows edema of foot by collagen.
Sham: normal mouse
Collagen: mouse administered collagen
Compound 18: mouse intraperitoneally injected with 25 mg/kg of compound 18

FIG. 18 is length of colon, and FIG. 19 is width of colon.

MODES FOR CARRYING OUT THE INVENTION

Figure 1:
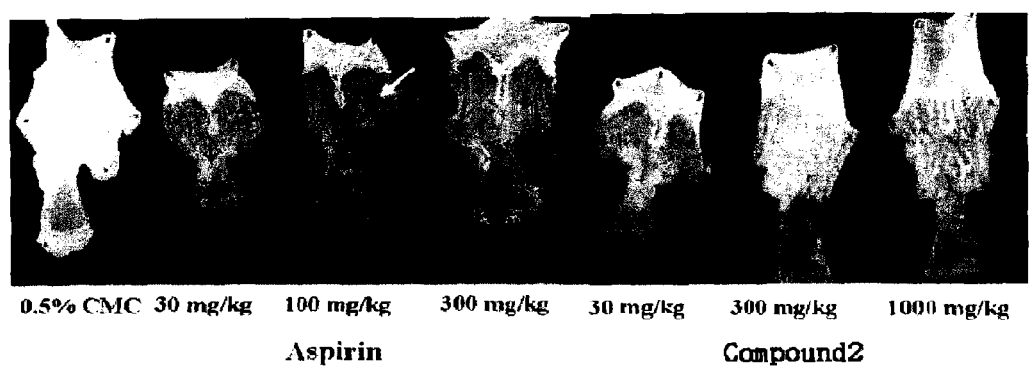
FIG. 1 shows that compound 2 did not cause damage to the gastric mucous membrane, which means that compound 2 is safe. Test samples were orally administered at different doses to evaluate the degree of the gastric mucous membrane damage. Aspirin was used as control.

Hereinafter, the present invention is described in considerable detail to help those skilled in the art understand the present invention. However, the following examples are offered by way of illustration and are not intended to limit the scope of the invention. It is apparent that various changes may be made without departing from the spirit and scope of the invention or sacrificing all of its material advantages.

Synthesis Example 1

Preparation of 2-hydroxy-5-[2-(4-trifluoromethyl-phenyl)-ethylamino]-benzoic acid (compound 2)

5-aminosalicylic acid (0.51 g, 3.90 mmole) was added to N,N-dimethylformamide (20.0 ml) at room temperature under nitrogen atmosphere, and the reaction mixture was stirred. Triethylamine (0.50 ml) and tetrabutylammonium iodide (10.1 mg) were added, and stirred for 30 minutes. Then, 1-(2-(bromoethyl)-4-trifluoromethyl)benzene was added, and stirred at room temperature for 3 hours. Ice was added to quench the reaction. Produced crystal was filtered, again stirred with acetone and hexane, and re-filtered. Filtered solid was dissolved in ethylacetate, washed with 0.5 N hydrochloric acid and brine, dried over magnesium sulfate anhydrous, and distilled in vacuo to give 0.54 g (21% yield) of 2-hydroxy-5-(4-(trifluoromethyl)phenylethylamino)benzoic acid.

$^1$H NMR (DMSO-$d_6$): 7.62 (d, 2H), 7.48 (d, 2H), 6.98 (d, 1H), 6.88 (q, 1H), 6.76 (d, 1H), 3.24 (t, 2H), 2.91 (t, 2H)<

Synthesis Example 2

Preparation of 2-hydroxy-5-[2-(4-trifluoromethyl-phenyl)-ethylamino]-benzoic acid potassium salt 2-hydroxy-5-[2-(4-trifluoromethyl-phenyl)-ethylamino]-benzoic acid (10 g, 30.7 mmole) produced in the synthesis example 1 was added to anhydrous ethanol (100 ml), and warmed up to 50° C. to completely dissolve. Then, the solution was cooled to 0° C. pH was adjusted to 6.8-7.0 with the solution of 85% potassium hydroxide (2.03 g, 30.7 mmole) and anhydrous ethanol (20 ml), and stirred at room temperature for 2 hours. Precipitated crystal was filtered and dried to give 10.4 g (93% yield) of 2-hydroxy-5-(4-(trifluoromethyl) phenylethylamino)benzoic acid potassium salt.

$^1$H NMR (DMSO-$d_6$): 7.62 (d, 2H), 7.48 (d, 2H), 6.98 (d, 1H), 6.90 (q, 1H), 6.84 (d, 1H), 3.24 (t, 2H), 2.91 (t, 2H)<

Synthesis Example 3

Preparation of 2-hydroxy-5-[2-(4-nitrophenyl)ethylamino]-benzoic acid

According to the similar procedure to Synthesis Example 1, by using 5-aminosalicylic acid (500 mg, 3.26 mmole) and 4-nitrophenylethyl bromide (900 mg, 3.92 mmole), 890 mg (50% yield) of 2-hydroxy-5-[2-(4-nitrophenyl)ethylamino]-benzoic acid was obtained as a pale yellow solid. Melting point 234-236° C.

Elemental analysis of $C_{15}H_{19}N_2O_5$

TABLE 1

|  | % C | % H | % N |
|---|---|---|---|
| Calculated | 59.60 | 4.67 | 9.27 |
| Found | 59.77 | 4.79 | 9.24 |

Synthesis Example 4

Preparation of 2-hydroxy-5-[3-(4-nitro phenyl)-n-propylamino]-benzoic acid

According to the similar procedure to Synthesis Example 1, by using 5-aminosalicylic acid (500 mg, 3.26 mmole) and 3-(4-nitrophenyl)propyl bromide (950 mg, 3.92 mmole), 520 mg (50% yield) of 2-hydroxy-5-[3-(4-nitrophenyl)-n-propylamino]-benzoic acid was obtained as a pale yellow solid. Melting point 229-231° C.

Elemental analysis of $C_{16}H_{16}N_2O_5$

TABLE 2

|  | % C | % H | % N |
|---|---|---|---|
| Calculated | 60.75 | 5.10 | 8.86 |
| Found | 60.77 | 5.07 | 8.89 |

Synthesis Example 5

According to the similar procedure to Synthesis Example 1, the other compounds were prepared. Analysis results were shown in table 3 below.

TABLE 3

| # | $^1$H-NMR(δ) |
|---|---|
| compound 3 | 7.54 (m, 4H), 7.20 (s, 1H), 6.59 (d, 1H), 6.47 (d, 1H), 3.19 (t, 2H), 2.90 (t, 2H) |
| compound 4 | 7.97 (s, 2H), 7.88 (s, 1H), 7.28 (s, 1H), 7.15 (t, 1H), 6.82 (d, 1H), 3.42 (t, 2H), 3.09 (t, 2H) |
| compound 5 | 7.91 (d, 1H), 7.58 (t, 1H), 7.51 (d, 1H), 7.43 (t, 1H), 7.10 (d, 1H), 6.64 (q, 1H), 6.51 (d, 1H), 3.21 (t, 2H), 3.04 (t, 2H) |
| compound 6 | 7.31 (d, 2H), 7.26 (d, 2H), 7.05 (s, 1H), 6.58 (d, 1H), 6.49 (d, 1H), 3.18 (t, 2H), 2.81 (t, 2H) |
| compound 7 | 7.31 (m, 2H), 7.11 (s, 1H), 6.94 (d, 1H), 6.87 (d, 1H), 6.74 (d, 1H), 3.17 (t, 2H), 2.87 (t, 2H) |
| compound 8 | 7.51 (d, 2H), 7.19 (d, 1H), 6.97 (t, 1H), 6.75 (t, 1H), 6.44 (d, 1H), 3.22 (t, 2H), 2.91 (t, 2H) |
| compound 9 | 7.94 (s, 1H), 7.64 (q, 2H), 7.45 (q, 2H), 7.10 (d, 1H), 3.48 (t, 2H), 3.21 (t, 2H) |
| compound 10 | 7.83 (t, 1H), 7.64 (d, 1H), 7.35 (t, 1H), 6.96 (q, 1H), 6.52 (t, 1H), 3.20 (t, 2H), 3.11 (t, 2H) |
| compound 11 | 7.32 (d, 1H), 7.14 (d, 2H), 6.82 (d, 2H), 6.78 (q, 1H), 6.64 (d, 1H), 3.79 (s, 3H), 3.24 (t, 2H), 2.80 (t, 2H) |
| compound 12 | 7.21-7.11 (m, 5H), 6.93 (d, 1H), 6.78 (d, 1H) 3.17 (t, 2H), 2.82 (t, 2H) |
| compound 13 | 7.27-7.11 (m, 5H), 6.95 (d, 1H), 6.81 (q, 1H), 6.70 (m, 1H), 2.97 (t, 2H), 2.64 (t, 2H), 1.82 (m, 2H) |
| compound 14 | 7.61 (d, 2H), 7.43 (d, 2H), 6.97 (s, 1H), 6.85 (t, 1H), 6.78 (d, 1H), 3.04 (t, 2H), 2.78 (t, 2H), 1.87 (m, 2H) |
| compound 15 | 7.17 (t, 3H), 7.02 (t, 2H), 6.94 (d, 1H), 6.78 (d, 1H), 2.99 (t, 2H), 2.63 (t, 2H), 1.82 (m, 2H) |
| compound 16 | 7.45 (q, 2H), 7.15 (d, 1H), 7.05 (d, 1H), 6.92 (q, 1H), 6.77 (d 1H), 2.96 (t, 2H), 2.66 (t, 2H), 1.82 (m, 2H) |
| compound 17 | 7.32 (s, 1H), 7.18 (d, 1H), 7.06 (s, 4H), 6.84 (d, 1H), 3.01 (t, 2H), 2.61 (t, 2H), 2.20 (s, 3H), 1.83 (m, 2H) |

Synthesis Example 6

Preparation of 2-acetoxy-5-[2-(4-trifluoromethyl-phenyl)-ethylamino]-benzoic acid (compound 18)

Compound 18 was prepared by the reaction scheme below.

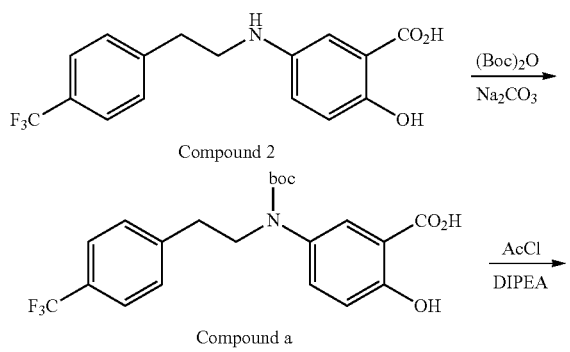

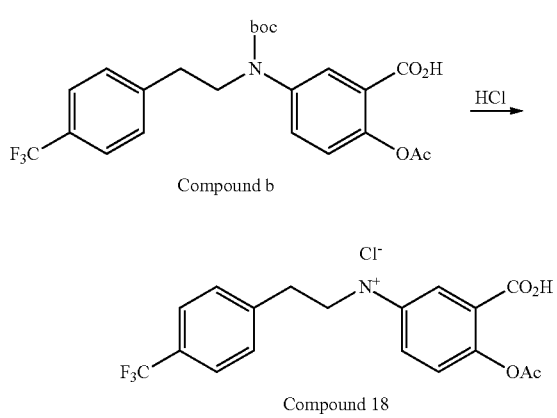

Compound b

Compound 18

Compound a: To a solution of compound 2 (50.0 g, 154 mmol) in 200 mL of $H_2O$:1,4-dioxane (1:1) at room temperature were added $Na_2CO_3$ (32.6 g, 307 mmol), di-tert-butyl dicarbonate (40.3 g, 185 mmol). After 8 hours stirring, additional di-tert-butyl dicarbonate (16.8 g, 76.9 mmol) was added. After additional 8 hours stirring at room temperature, the reaction mixture was neutralized (pH ~6) with aqueous 2 N HCl. The resulting mixture was extracted with ethyl acetate (2×200 mL). The combined organic phase was washed with brine (100 mL), dried over $MgSO_4$ and filtered. Concentration gave compound a as yellow foam. Crude a was used without further purification.

$^1$H NMR (400 MHz, $CDCl_3$) δ 10.52 (1H, br S), 7.53 (d, 2H, J=8 Hz), 7.53 (br, 1H), 7.28 (d, 2H, J=8 Hz), 7.26 (br, 1H), 6.94 (d, 1H, J=8.8 Hz), 3.85 (t, 2H, J=7.2 Hz), 2.94 (t, 2H, J=7.2 Hz), 1.43 (br s, 9H).

Compound b: To a solution of compound a obtained above in dichloromethane (200 mL) were added N,N-diisopropylethylamine (80.3 mL, 461 mmol) and acetyl chloride (21.9 mL, 307 mmol) at 0° C. The reaction mixture was warmed to room temperature and stirred for 5 hours. Aqueous 1 N HCl (100 mL) was added to the reaction mixture. The layers were separated and the aqueous layer was extracted with dichloromethane (100 mL). The combined organic layer was washed with brine (100 mL), dried over $MgSO_4$, filtered and concentrated. Recrystallization of the crude product in diethyl ether gave 22 (51.5 g, 71.7% for 2 steps) as a white solid.

$^1$H NMR (400 MHz, $CDCl_3$) δ 7.82 (br s, 1H), 7.54 (d, 2H, J=8 Hz), 7.38-7.24 (m, 1H), 7.28 (d, 1H, J=8 Hz), 7.08 (d, 1H, J=7.6 Hz), 3.91 (t, 2H, J=7.2 Hz), 2.98 (t, 2H, J=7.2 Hz), 2.34 (s, 3H), 1.42 (br s, 9H).

Compound 18: A solution of compound b (51.5 g, 110 mmol) in dichloromethane (200 mL) at 0° C. was treated with 4 N HCl in 1,4-dioxane (200 mL). The reaction mixture was warmed to room temperature. After 5 hours stirring, the suspension was concentrated. The residue was triturated in diethyl ether (500 mL). Filtration and washing with dichloromethane (500 mL) and with diethyl ether (500 mL) gave compound 18 (46.0 g, 82.5 mmol, 92.3%) as a white solid.

$^1$H NMR (400 MHz, DMSO-$d_6$) δ 7.66 (d, 2H, J=7.6 Hz), 7.52 (d, 2H, J=7.6 Hz), 7.15 (s, 1H), 6.91 (d, 1H, J=8.6 Hz), 6.85 (d, 1H, J=8.6 Hz), 3.32 (t, 2H, J=7 Hz), 2.95 (t, 2H, J=7 Hz), 2.18 (s, 3H)); LCMS calc. for $C_{18}H_{16}F_3NO_4$ (M+H$^+$): 368, found 368.

Example 1

Anti-Inflammatory Effect in Cell 1-1. Suppressing Effect on Production of NO

Inhibiting effect of the 2-hydroxybenzoic acid derivative according to the present invention on NO, inflammatory factor intervening inflammation reaction was evaluated. BV2 microglia cell line was treated with lipopolysaccharide (LPS), a inflammation-inducing material of bacteria toxin, with inclusion of 10 uM, 30 uM or 100 uM of the present compound. After 24 hours of incubation, 50 ul of culture medium was collected in 96-well plate. Then, 50 ul of Griess reagent was added and incubated for 10 minutes at room temperature. The absorbance was evaluated by ELISA reader at 540 nm. $IC_{50}$ value of each compound was calculated and shown in the below table 4 ("NO in BV").

As shown in the below table 4, $IC_{50}$ values of compound 9 and 14 were 1.79 uM and 6.7 uM, respectively, which are on a highest level. When inhibiting effect on the production of NO was evaluated as $IC_{50}$ value, most compounds had lower values than 100 uM. As shown in results, the 2-hydroxybenzoic acid derivative of the present invention is thought to be useful as anti-inflammatory agent because the compound suppresses the activity of NO intervening inflammation reaction.

1-2. Suppressing Effect on Gene Expression

Effects of the 2-hydroxybenzoic acid derivatives on iNOS gene expression in BV2 cell line were evaluated. 100 mm dish was inoculated with $1×10^6$ cells of BV2 cell line, and treated with both LPS, inflammation-inducing material, and 1~100 uM of the 2-hydroxybenzoic acid derivative of the present invention, together, in regular concentration interval. After 24 hours of incubation, RNA was extracted. Extracted RNA was used in reverse transcription and polymerase chain reaction, and expression patterns of TNF-alpha, IL-1beta and iNOS were compared. Results were shown in the below table 4.

As shown in the table 4, when gene expressions of inflammatory cytokines are compared to control (LPS treatment), expression of TNFalpha gene was decreased 63.24% by compound 2, 77.05% by compound 8, and 61.67% by compound 9. Expression of IL-1beta gene was evaluated to be decreased 75.1% by compound 2, 67.7% by compound 5, and over 50% by compounds 8, 9, 10 and 14. Furthermore, compounds 2, 5, 8, 10, 15 and 17 suppressed expression of iNOS gene by more than 50%.

TABLE 4

| Compound No. | $IC_{50}$ (uM) NO in BV | % Inhibition (in 100 uM) TNF-alpha | IL-1beta | iNOS |
|---|---|---|---|---|
| 1 | 182.99 | ND | ND | ND |
| 2 | 24.26 | 63.2 | 75.1 | 105.5 |
| 3 | 26.14 | ND | ND | ND |
| 4 | 6.25 | ND | ND | ND |
| 5 | 12.45 | 38.7 | 67.7 | 108.5 |
| 6 | >100 | ND | ND | ND |
| 7 | 23.69 | ND | ND | ND |
| 8 | 63.25 | 77.1 | 56.9 | 113.8 |
| 9 | 1.79 | 61.7 | 76.7 | 17.8 |
| 10 | 20.67 | ND | 83.6 | 88.9 |
| 11 | 132.15 | ND | ND | ND |
| 12 | 18.62 | ND | 41.8 | 43.7 |
| 13 | 85.43 | 43 | ND | 15.5 |
| 14 | 6.7 | 38.9 | 80.4 | 44.3 |
| 15 | 20.34 | 37.4 | 35.1 | 86.2 |
| 16 | 51.78 | ND | ND | ND |
| 17 | 26.5 | 20.8 | ND | 111.1 |
| 18 | 21.63 | ND | ND | ND |

In the table 4, the term 'ND' means "not determined."

1-3. Suppressing Effect on Production of Cytokine

Effects of the 2-hydroxybenzoic acid derivatives on production of cytokine in BV2 cell line were evaluated. 24-well plate was inoculated with $1\times10^6$ cells of BV2 cell line, and treated with both LPS, inflammation-inducing material, and 100 uM of sample (the 2-hydroxybenzoic acid derivative or comparative drug), together. After 24 hours of incubation, culture medium was collected. The levels of cytokines, TNF-α and IL-6, in the medium were evaluated by ELISA method. Results were shown in the below table 5.

As shown in the table 5, when compared to control (LPS treatment), the level of TNF-α produced by LPS was reduced 62.26% by compound 2, 31.90% by compound 3, and 62.6% by compound 14. However, comparative drugs (ibuprofen and aspirin) did not showing reducing effect at the same concentration. Similarly, the level of IL-6 was apparently decreased by compound, but the level of IL-6 was little reduced by ibuprofen and aspirin.

TABLE 5

| compound No | TNF-α % Inhibition | IL-6 % Inhibition |
|---|---|---|
| 2 | 62.26 | 70.31 |
| 3 | 31.90 | 33.06 |
| 4 | 18.71 | ND |
| 14 | 62.60 | ND |
| Ibuprofen | No effect | No effect |
| Aspirin | No effect | 22.18 |

In the table 5, the term 'ND' means "not determined."

Example 2

Basic Toxicity Test

Single-dose toxicities of the 2-hydroxybenzoic acid derivatives were evaluated. Results were shown in FIG. 32.

Figure 32:
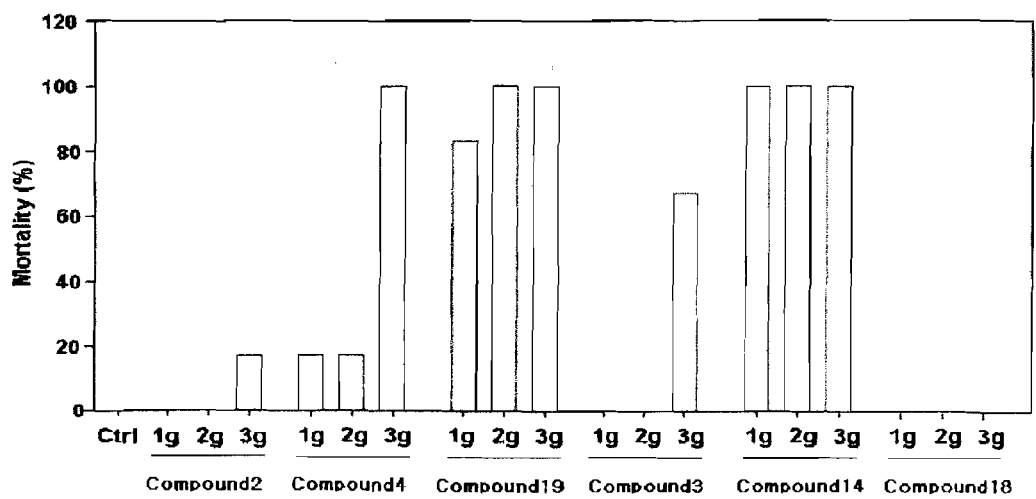
FIG. 32 is results of single dose toxicity testing of some 2-hydroxybenzoic acid derivatives according to the present invention.

As shown in FIG. 32, $LD_{50}$ of compounds 2 and 18, preferable examples of the present invention, were more than 3 g/kg, which means that the compounds have good safety. Chemical 19 had 0.5-1 g/kg of $LD_{50}$, that is, chemical 19 showed relatively worse safety. In addition, compound 4 showed much better effect in anti-inflammatory test, etc., but compound 4 did not show dose-dependent result in toxicity test because the compound caused sudden death of mouse at 3 g/kg of dose test. Compounds 3 and 14 have the similar chemical structure with compound 2, and show the similar therapeutic effects with compound 2 in anti-inflammatory test, but the compounds show high toxicity or dose-independent toxicity.

Example 3

Safety Test about Induction of Gastric Mucous Membrane Damage

Conventional NSAIDs have side effects causing damages to the gastric mucous membrane. Therefore, it was evaluated whether compound 2 having anti-inflammatory effect causes the gastric damage or not. 30, 100 or 300 mg/kg of aspirin was orally administered as control. Compound 2 of the present invention did not cause the gastric side effect even when 1,000 mg/kg of compound 2 was orally administered. From this result, it is believed that the 2-hydroxybenzoic acid derivative of the present invention is very safe (FIG. 1).

Figure 2:
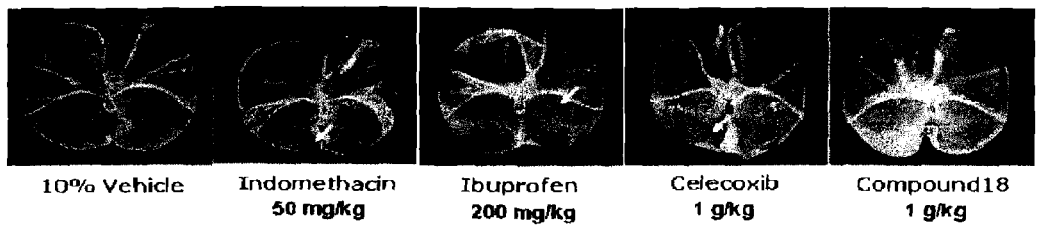
FIG. 2 is results showing degrees of the gastric mucous membrane damage. Test samples were orally administered at indicated doses. Compound 18 did not cause gastric mucous membrane damage at high dose. Indomethacine, ibuprofen and celecoxib were used as control.

In addition, the safety of compound 18 was evaluated by comparison with indomethasin and ibuprofen (other NSAIDs) and celecoxib (a selective COX-2 inhibitor). Compound 18 did not cause damage to gastric mucous membrane even in the high dose of oral administration (FIG. 2).

Example 4

Cell-Protecting Effect

Figure 3:
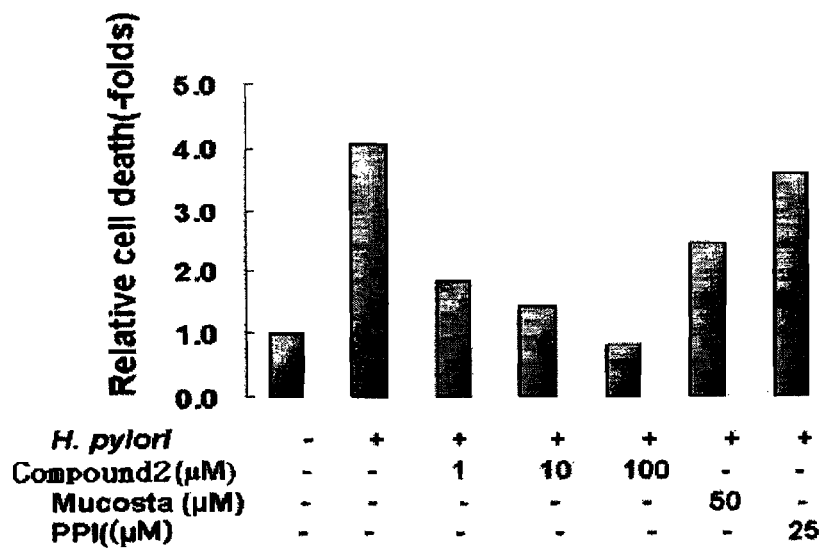
FIG. 3 is results showing cell-protecting effect of compound 2 on gastric mucous membrane damage induced by Helicobacter. Helicobacter (43504, $5 \times 10^6$ cfu/ml) was administered to cultured AGS (human gastric cancer) cell, alone or with sample having indicated concentration. MTT analysis method was used to evaluate the survival rate of gastric mucous membrane cell 24 hours after administration.
Figure 4:
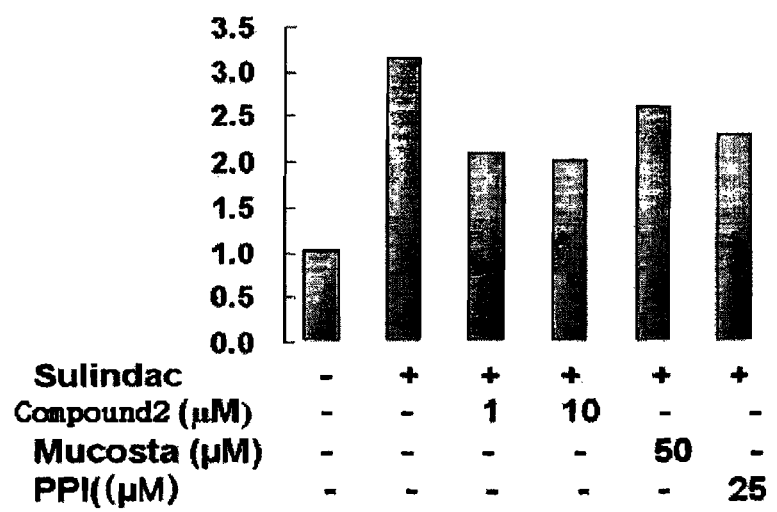
FIG. 4 is results showing cell-protecting effect of compound 2 on gastric mucous membrane damage induced by sulindac, a NSAID. 100 uM of sulindac was administered to cultured AGS cell, alone or with sample having indicated concentration. MTT analysis method was used to evaluate the survival rate of gastric mucous membrane cell 16 hours after administration.
Figure 5:
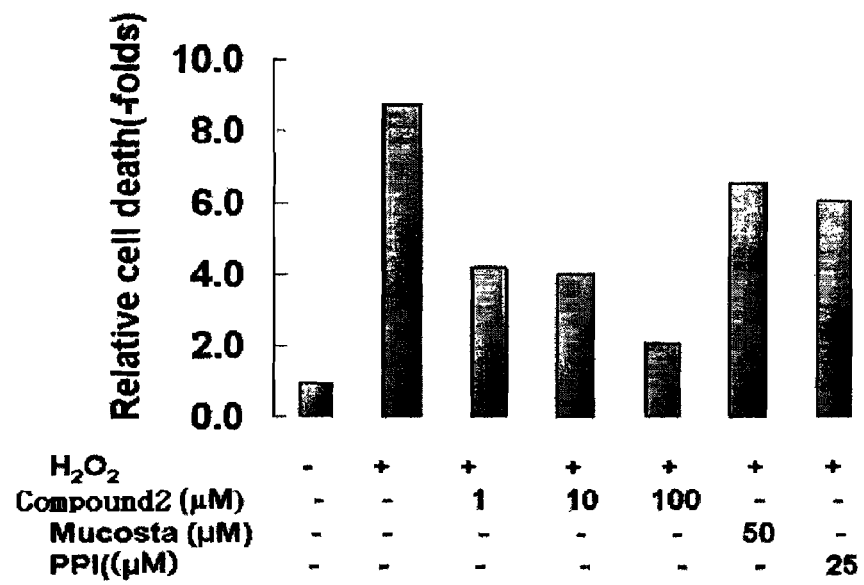
FIG. 5 is results showing cell-protecting effect of compound 2 on gastric mucous membrane damage induced by $H_2O_2$, oxidative stress. Cultured AGS cell was treated with 100 uM of $H_2O_2$ for 8 hours, alone or with sample having indicated concentration, and was washed with culture medium. MTT analysis method was used to evaluate the survival rate of gastric mucous membrane cell 24 hours later.
Figure 6:
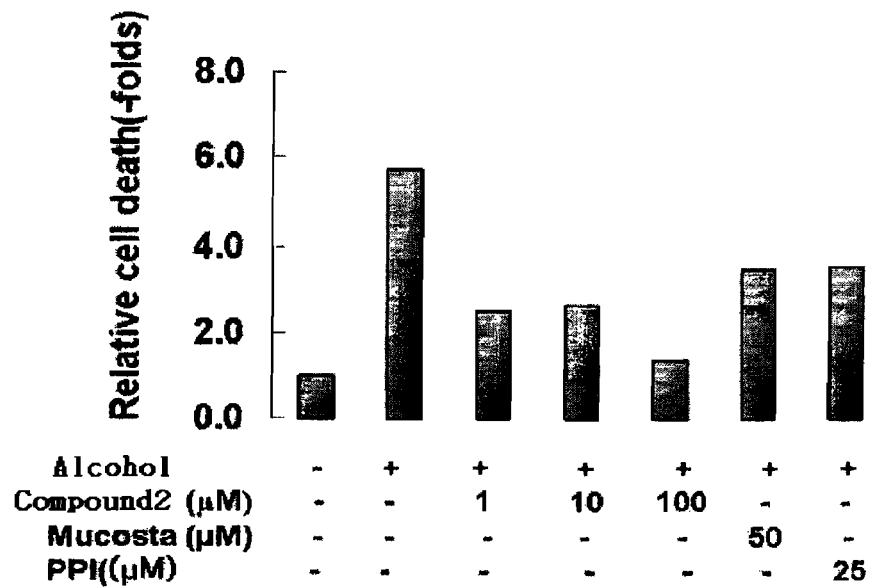
FIG. 6 is results showing cell-protecting effect of compound 2 on gastric mucous membrane damage induced by alcohol (ethanol). Cultured AGS cell was treated with 25 mM of alcohol for 24 hours, alone or with sample having indicated concentration. Then, MTT analysis method was used to evaluate the survival rate of gastric mucous membrane cell.

Cell-protecting effect of the 2-hydroxybenzoic acid derivative of the present invention was evaluated. AGS cell line (human gastric cancer cells, $1\times10^5$ cells) was inoculated onto 96-well plate. Then, death of gastric mucous membranes was caused by 24 hour-treatment of *Helicobacter* (FIG. 3), 16 hour-treatment of sulindoc (FIG. 4), 8 hour-treatment of $H_2O_2$ (FIG. 5) or 24 hour-treatment of ethanol (FIG. 6). In addition, some of AGS cell line were together treated with 10 uM, 30 uM or 100 uM of compound 2. The cell lines were incubated for 24 hours. MTT solution was added to each well, and incubated 4 hours at 37° C. After than, the absorbance was analyzed by ELISA reader at 540 nm, and the survival rate of gastric mucous membranes cell was calculated. In results, 1 uM and 10 uM of compound 2 showed more than 50% of cell-protecting effect, and 100 uM of compound 2 showed more than 70% of cell-protecting effect in most cell death models.

Figure 7:
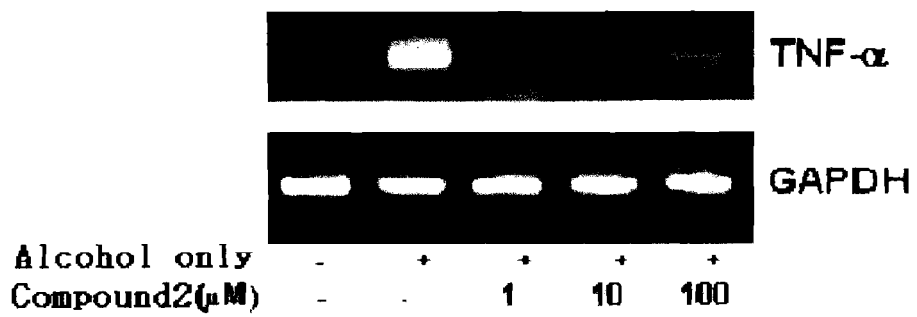
FIG. 7 is a picture showing the expression degree of TNF-α mRNA. Cultured AGS cell was treated with 25 mM of alcohol for 24 hours, alone or with compound 2 having indicated concentration. Then, mRNA was extracted and evaluated by RT-PCR method.

As one marker of inflammation, the expression level of TNF-α mRNA was evaluated by RT-PCR method. Samples treated with ethanol for 24 hours were used. 1-100 uM of compound 2 completely suppressed the expression of TNF-α mRNA (FIG. 7).

From these results, the 2-hydroxybenzoic acid derivative of the present invention is thought to be effectively used for suppressing inflammation disease, particularly, protecting cell and suppressing inflammation in gastritis caused by several reasons. Furthermore, the 2-hydroxybenzoic acid derivative of the present invention showed better effect than mucosta and PPI, which are known as therapeutic agent for treating inflammation.

Example 5

Figure 8:
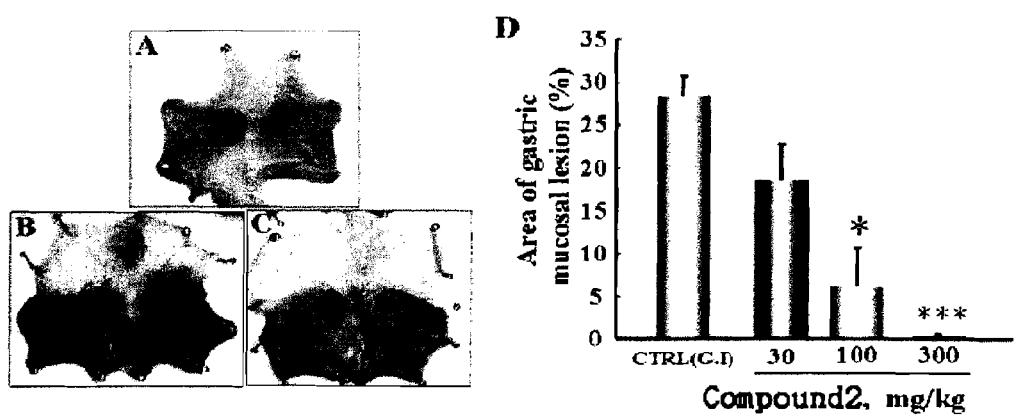
FIG. 8 is results showing protecting effect of compound on gastrointestinal bleeding caused by alcohol/hydrochloric acid (EtOH/HCl). A is a picture of normal rat stomach. B is a picture of rat stomach, wherein gastrointestinal bleeding was caused by oral administration of 60% EtOH/150 mM HCl after 200~250 g of rat was fasted for 24 hours. C is a picture of rat stomach, wherein rat was pre-treated with compound 230 minutes before administration of alcohol/HCl, and stomach was taken out 90 minutes after gastrointestinal bleeding. D is a graph quantifying damaged area to evaluate the degree of stomach injury.

Protecting Effect on Gastrointestinal Bleeding 5-1. Gastritis Induced by Alcohol and Hydrochloric Acid Effect of the 2-hydroxybenzoic acid derivative on gastritis induced by alcohol and hydrochloric acid was evaluated. 200~250 g of male SD rat was fasted for 24 hours, and 60% EtOH/150 mM HCl was orally administered to induce gastric bleeding (gastric injury). Compound 2 was orally administered according to indicated dose 30 minutes before the gastric bleeding, and stomach was taken out 90 minutes after gastric bleeding to evaluate the degree of gastric injury. In results, the compound 2 protected stomach against gastric bleeding induction, and did not show any toxicity. Results were shown in FIG. 8.

5-2. Alcoholic Gastritis

Figure 9:
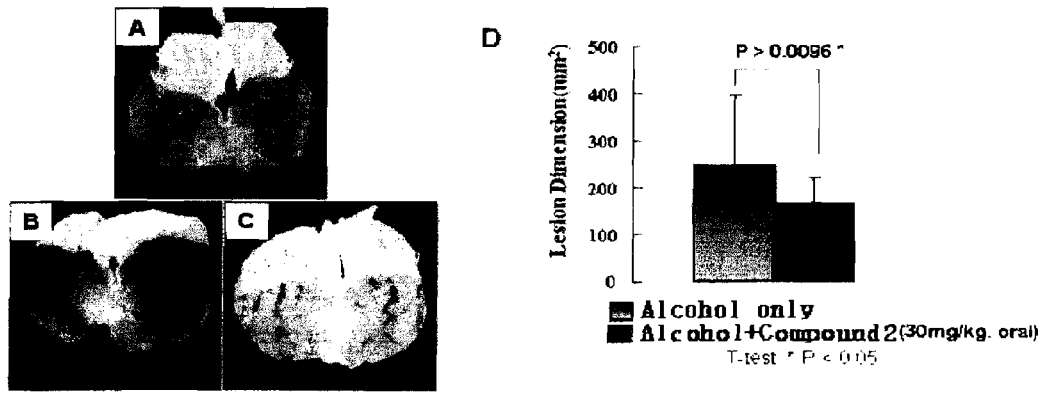
FIG. 9 is results showing protecting effect of compound 2 on alcoholic gastritis. A is a picture of normal rat stomach. B is a picture of rat stomach, wherein gastrointestinal bleeding was caused by oral administration of ethanol (4 ml/kg) after 250 g of rat was fasted for 24 hours. C is a picture of rat stomach, wherein rat was pre-treated with compound 2 1 hour before induction of gastrointestinal bleeding, and stomach was taken out 90 minutes after gastrointestinal bleeding. D is a graph quantifying the degree of stomach injury.

Effect of the 2-hydroxybenzoic acid derivative on alcoholic gastritis was evaluated. 250 g of rat was fasted for 24 hours, and alcohol was orally administered to cause gastric bleeding (B). Some rats were pre-treated with compound 21 hour before the administration of alcohol, and the rat showed significantly reduced gastric bleeding (C). Quantified results were shown in FIG. 9 (D). From these results, the compound 2 of the present invention is thought to have strong protecting effect on alcoholic gastritis.

Treatment of alcoholic gastritis is known to be more difficult than gastritis caused by other reasons because it is not easy to be treated even with inhibitor of gastric juice secretion or enhancer of gastric protecting factor. This is because alcohol causes the disease by the types of directly mediating toxicity and inflammation, inducing bleeding, etc. The compound 2 of the present invention is thought to significantly reduce this type of direct toxicity of alcohol.

5-3. Gastritis Caused by NSAID

Figure 10:
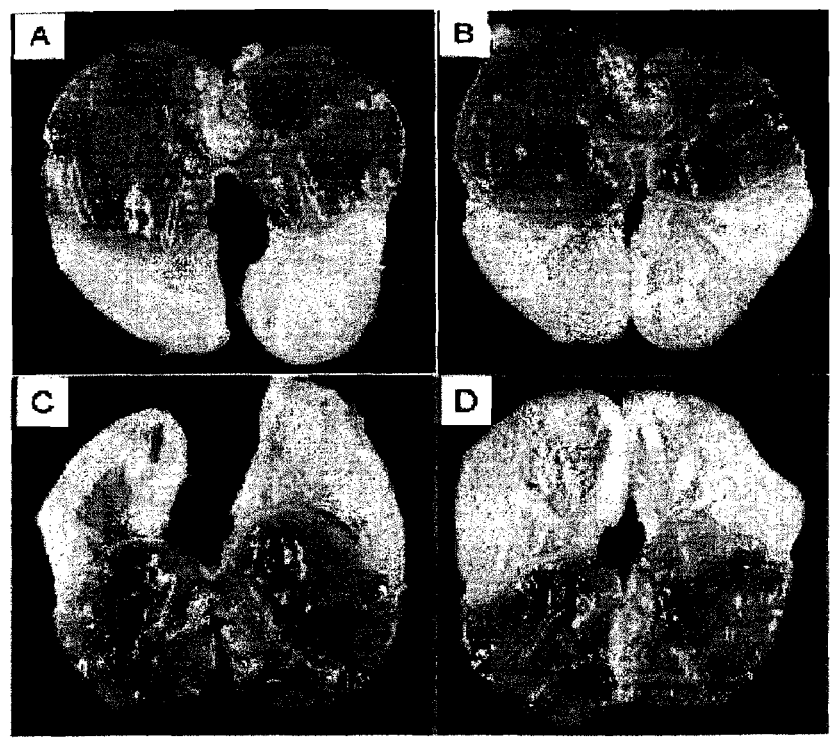
FIG. 10 is results showing protecting effect of compound 2 on gastritis induced by NSAID. 250 g of rat was fasted for 24 hours, and indomethacin was orally administered to cause gastrointestinal bleeding (A and C). Compound 2 was administered 1 hour before administration of NSAID (B and D), and stomach was taken out 6 hours (A and B) or 12 hours (C and D) after gastrointestinal bleeding.
Figure 11:
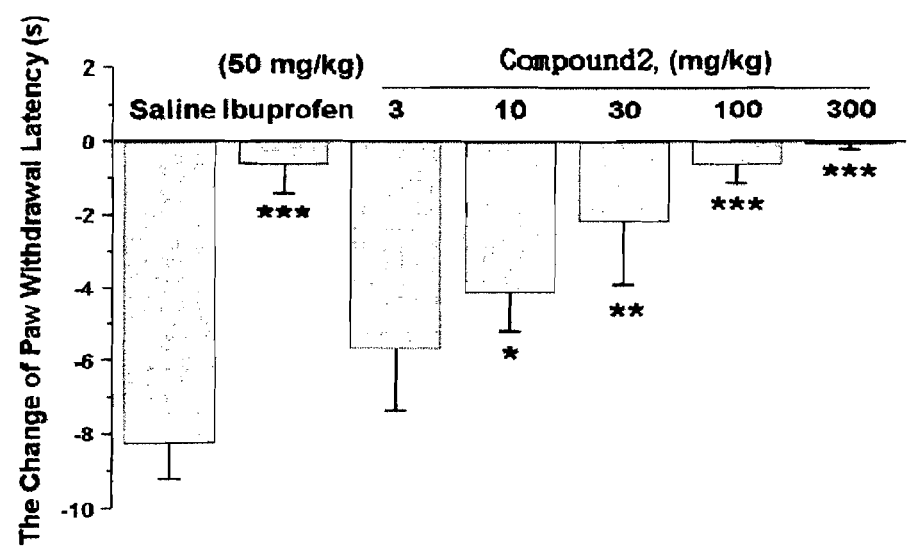
FIG. 11 is results showing efficacy of compound 2 through thermal hyperalgesia induced by carrageenan, one of arthritis animal models. 2% carrageenan was intradermally injected into hindpaw of rat to induce thermal hyperalgesia. Compound 2 was orally administered, and ibuprofen was used as comparative example.

Effect of the 2-hydroxybenzoic acid derivative on NSAID-induced gastritis was evaluated. Compound 2 showed excellent protecting effect on stomach (B and D of FIG. 10) in both weak gastric damage model (A of FIG. 10) induced by NSAID (indomethacine) 6 hour-administration and severe gastric damage model (C of FIG. 10) induced by indomethacine 12 hour-administration.

Example 6

Efficacy Test in Arthritis Animal Model 6-1. Inflammation Model Induced by Carrageenan: Evaluation of Analgesic Effect Analgesic effect of compound 2, one example of the 2-hydroxybenzoic acid derivative, was evaluated in arthritis model. 2% carrageenan was intradermally injected into left pes of rat, and 3-300 mg/kg of compound 2 was orally administered to evaluate effect of compound 2 on thermal hyperalgesia of arthritis model. Results were shown in FIG. 10.

Compound 2 decreased thermal hyperalgesia in a dose-dependent manner. 300 mg/kg of compound 2 reduced thermal hyperalgesia by over 90%. In addition, the equivalent level of decreasing effect with 50 mg/kg of ibuprofen, a known anti-inflammatory agent, was shown in group having 100 mg treatment of compound 2.

6-2. Inflammation Model Induced by Zymosan: Evaluation of Cytokine

Figure 12:
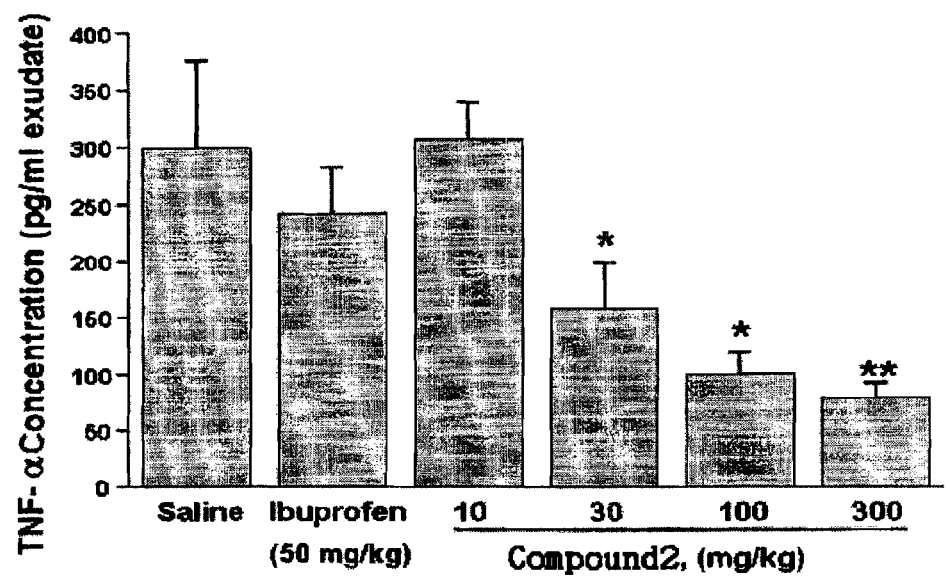
FIG. 12 is results showing efficacy of compound 2 through the levels of TNF-alpha induced by zymosan, one of arthritis animal models. 1% zymosan was administered with air pouch, and compound 2 was once orally administered according to indicated dose 1 hour before administration of zymosan. The level of TNF-alpha in an exudation of air pouch was evaluated by ELISA method 4 hours later.
Figure 13:
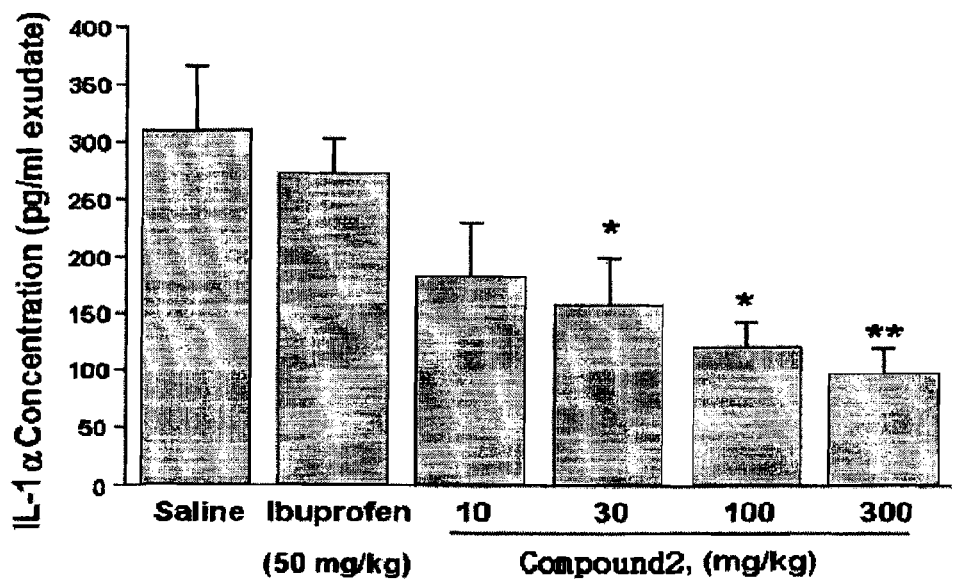
FIG. 13 is graphs showing how much compound 2 decreases the level of IL-1alpha induced by zymosan, one of arthritis animal models. 1% zymosan was administered with air pouch, and compound 2 was once orally administered according to indicated dose 1 hour before administration of zymosan. The level of IL-1alpha in an exudation of air pouch was evaluated by ELISA method 4 hours later.

Anti-inflammation effect of compound 2 in arthritis model was evaluated with zymosan. 0.5 ml of 1% zymosan was administered with air pouch, and 3-300 mg/kg of compound 2 was once orally administered 1 hour before administration of zymosan. Edema, a main symptom of arthritis, and the level of cytokine were observed 4 hours later. In results, over 30 mg/kg of compound 2 decreased the level of TNF-alpha more than control, and decreased the level up to 300 mg/kg in a dose-dependent manner. As comparative example, ibuprofen (50 mg/kg), a well-known anti-inflammatory drug, was used (FIG. 12). Similarly, IL-1alpha also was decreased in a dose-dependent manner (FIG. 13). From these results, the 2-hydroxybenzoic acid derivative of the present invention is thought to be useful for treating inflammatory disease, particularly arthritis.

6-3. Animal Model Evaluation of Arthritis Induced by Collagen

Figure 14:
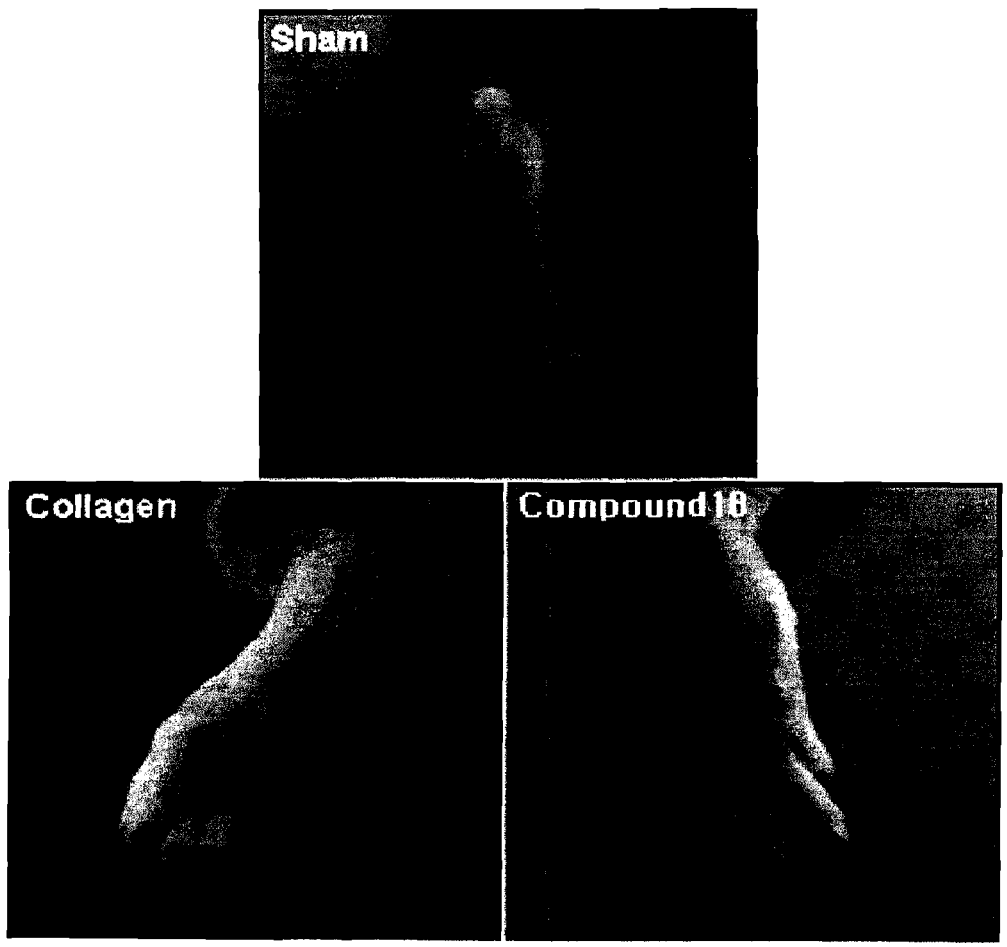
FIG. 14 is results showing efficacy through arthritis animal model induced by collagen.
Figure 15:
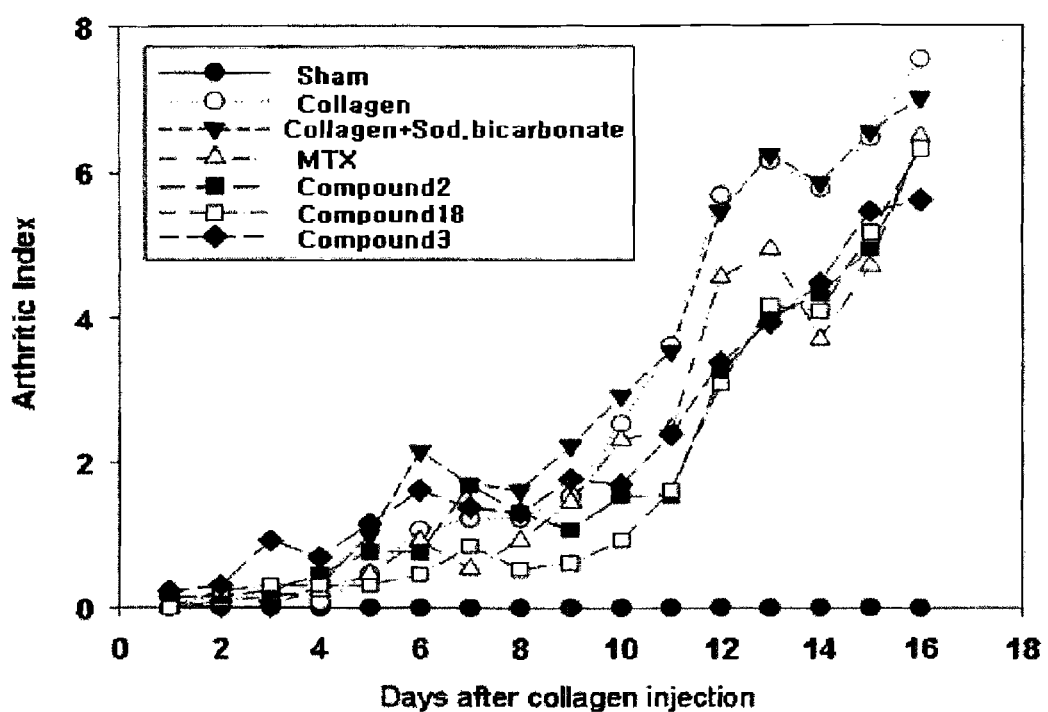
FIG. 15 is results showing efficacy through arthritis animal model induced by collagen. 25 mg/kg of compound 2, 3 or 18, or methotrexate (control, MTX, 1 mg/kg/week) was intraperitoneally injected after administration of collagen. Then, mice were observed with the naked eye for 4 weeks, and results were evaluated by arthritis index.

To evaluate the efficacy of the 2-hydroxybenzoic acid derivative, collagen-induced arthritis model (rheumarthritis animal model) was used. Bovine type II collagen was mixed with complete Freund's adjuvant to make an emulsion, and the emulsion was intradermally injected into the origin site of 8~10 week-old DBA/1LacJ mouse tail. Intradermal boosting was performed by the same method 2 weeks later. 25 mg/kg/day of compounds 2, 3 and 18, 1 mg/kg/week of methotrexate (comparative example) or 10% vehicle (control) were intraperitoneally injected one week after the second intradermal injection of collagen (FIG. 15). Pictures of foot edema of normal rat (sham), collagen-administered rat (collagen) and compound 18-administered rat (compound 18, 25 mg/kg/day injection) were shown in FIG. 14.

Figure 16:
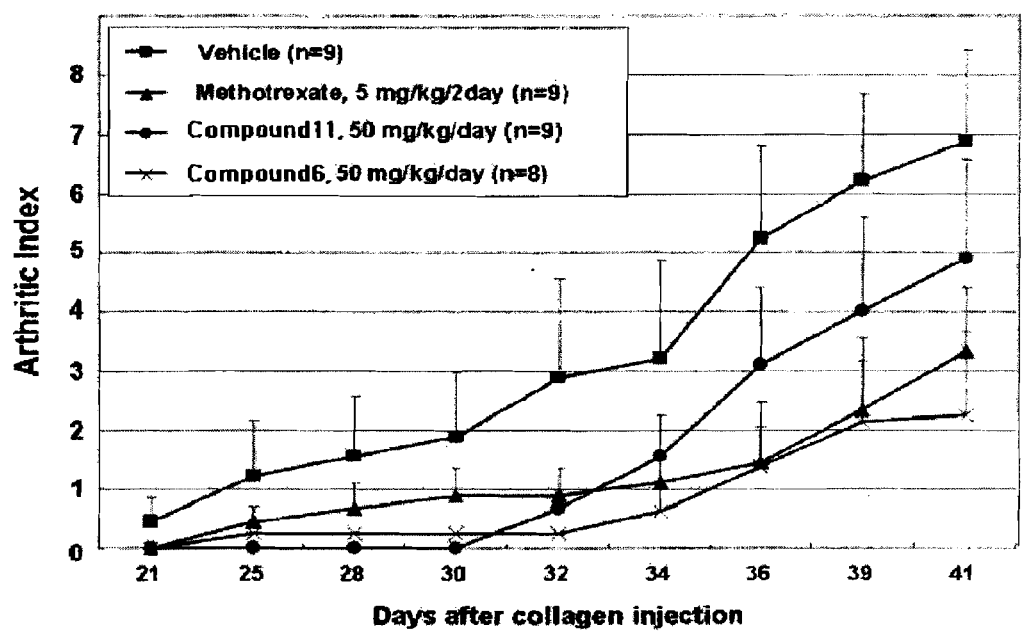
FIG. 16 is results showing efficacy of compounds 6 and 11 through arthritis animal model induced by collagen. Collagen was intradermally injected two times with 2 week-interval. One week later, compound 6, compound 11 and methotrexate (control) were intraperitoneally injected. Then, the animals were observed everyday for 2-3 weeks, and results was evaluated by arthritis index.

In addition, 50 mg/kg/day of compounds 6 and 11, and 5 mg/kg/2 days of methotrexate (comparative example) were intraperitoneally injected. Phosphate buffered saline was injected as control (FIG. 16). For 2~3 weeks, the degree of arthritis was observed everyday, and the result was evaluated according to the below arthritic index using edema. As shown in results of arthritic index, compounds 2, 3 and 18, and compounds 6 and 11 showed an apparent reducing effect (FIGS. 15 and 16).

—Arthritic Index—

4 paws were evaluated as from 0 to 4 point, Total points: 16

0 point—normal paw 1 point—mild edema and flare limited to tarsal bone 2 points—mild edema and flare extending from ankle joint to tarsal bone 3 points—middle edema and flare extending from ankle joint to metatarsal bone 4 points—edema and flare extending from ankle joint to total digit Example 7

Efficacy Test in Inflammatory Intestinal Disease Animal Model

5% dextran sulfate sodium (DSS) model was used as inflammatory intestinal disease animal model. 5% DSS mixed with water was orally administered. 5% DSS model causes damage to epithelial cell, and ulcer in left colon and the decrease of colon length are mainly observed in the model. This model is simple and reproductive, and can regulate the degree of inflammation according to dose. Therefore, this model is often used for evaluating drug candidates.

DSS is continuously administered in water bottle. The 2-hydroxybenzoic acid derivative was suspended in 10% vehicle, and orally administered.

Figure 17:
FIG. 17 is results showing efficacy through 5% dextran sulfate sodium (DSS) model, inflammatory intestinal disease animal model. After treatment of DSS, 10, 25 or 50 mg/kg of compound 18 suspended in 10% vehicle was orally administered. Sham means colon of normal mouse, DSS means colon mouse treated with 5% DSS. The others are pictures of colon of mice administered with compound 18 at indicated dose.
Figure 18:
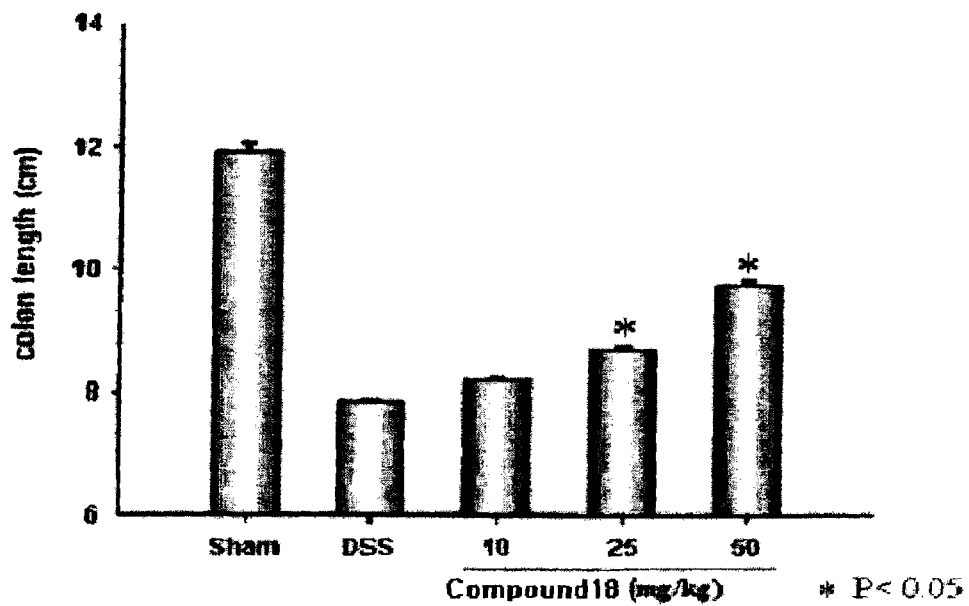
FIGS. 18 and 19 are graphs quantifying results of FIG. 17.
Figure 19:
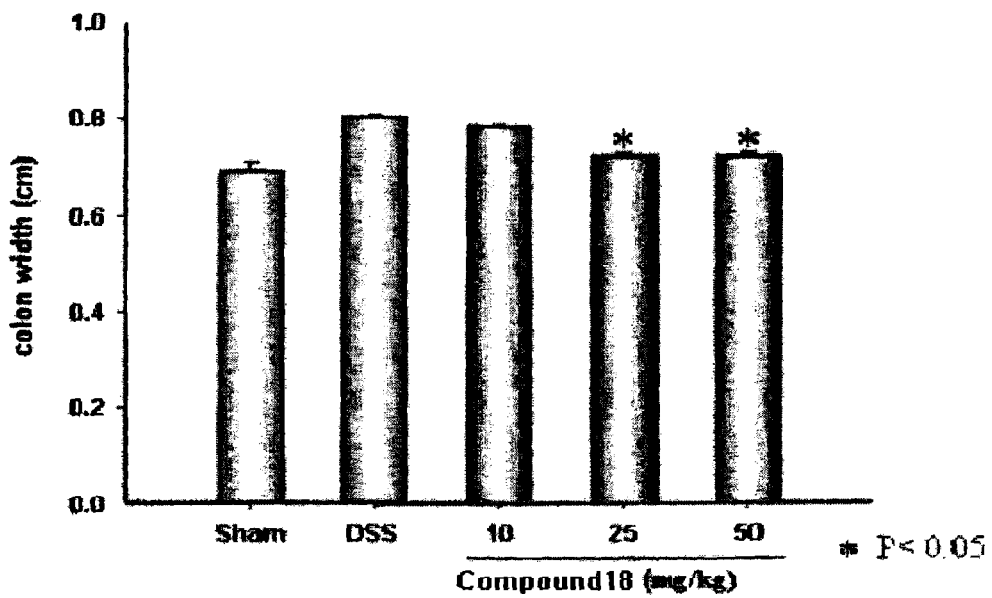

Administration of DSS changed the length and width of colon. Treatment of compound 18 significantly changed the length and width of the colon (FIGS. 17, 18 and 19). This result means that the compound of the present invention has protective effect in this colitis model.

Figure 20:
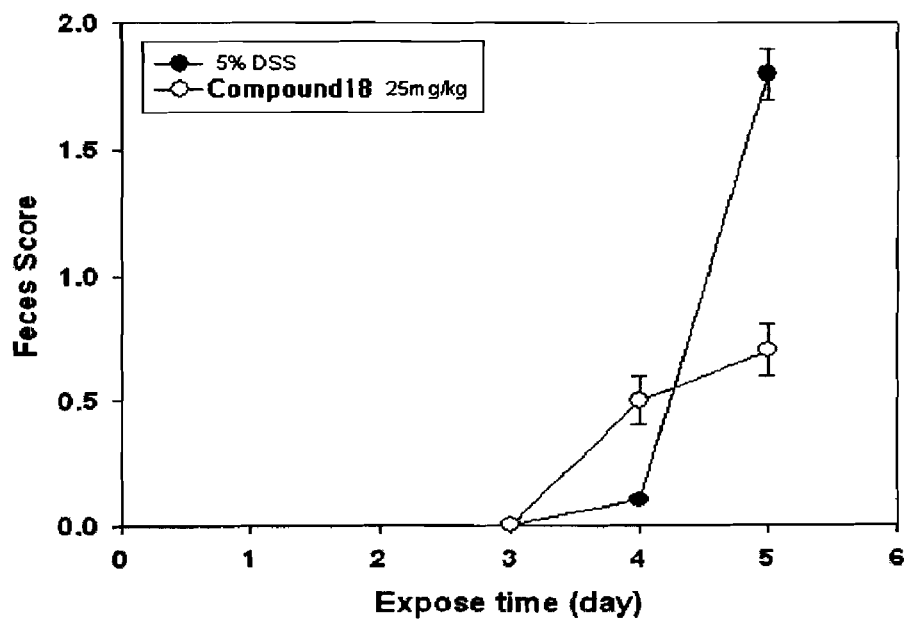
FIG. 20 is an efficacy test result of compound 18 using DSS. After treatment of DSS, compound 18 (25 mg/kg) suspended in 10% vehicle was orally administered. After that, bloody excrement by colon injury, diarrhea and the degree of dirtiness were evaluated as feces score.

In addition, bloody excrement, diarrhea and the degree of dirtiness were evaluated everyday as feces condition. Both sulfasalazine and compound 18 significantly decreased feces score compared to group treated with DSS only (FIG. 20).

Example 8

Efficacy Test in Acute Pancreatitis Animal Model

Figure 21:
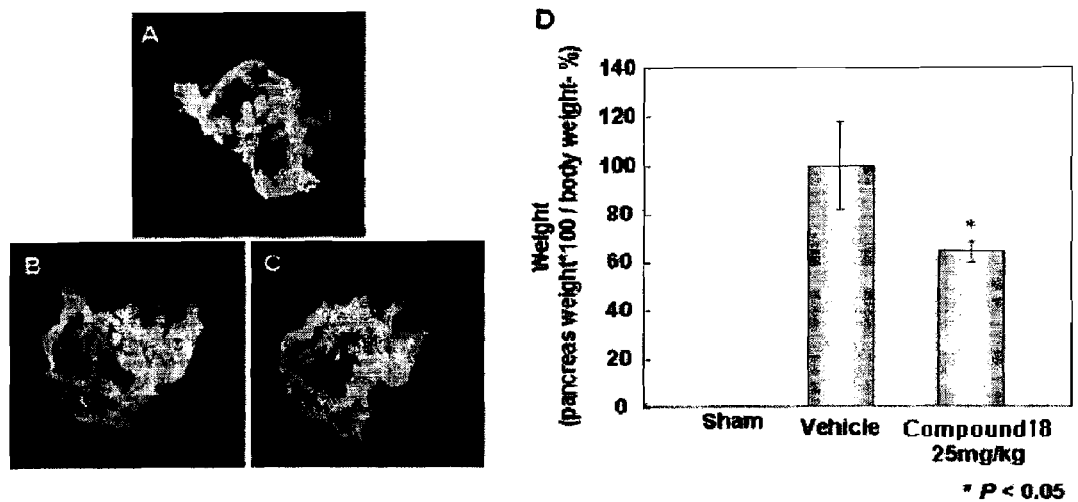
FIG. 21 is efficacy test results using acute pancreatitis model induced by cerulein. 50 ug/kg of cerulein was administered. Two hours later, edema was induced by administration of LPS. A-C are picture results, and D is graphs showing the weight of pancreas.
A: normal wistar rat
B: wistar rat administered cerulein
C: wistar rat administered compound 18 (25 mg/kg)

Cerulein-induced pancreatitis model was used as acute pancreatitis model. Cerulein is an analog of cholecystokinin and a hormone causing secretion of pancreatic digestive enzyme in pancreas. Digestive enzyme was over-secreted into pancreas by intraperitoneal injection of cerulein (50 ug/kg). LPS was injected 2 hours later to induce edema. When cerulein was administered, massive edema was observed on the basis of spleen. In addition, when 25 mg/kg of compound 18 was administered, the edema was decreased (FIG. 21). D of FIG. 21 is results showing the pancreas weight increased by the edema. Group treated with compound 18 had significantly reduced pancreas weight.

Figure 22:
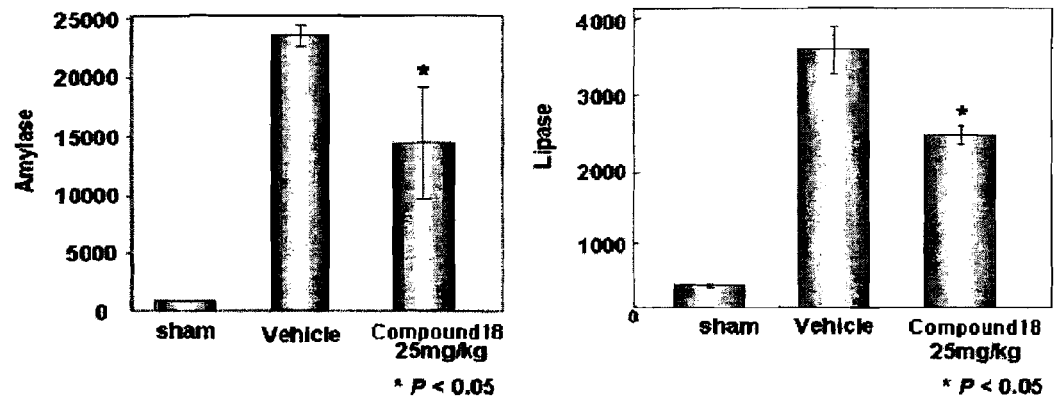
FIG. 22 is efficacy test results using acute pancreatitis model induced by cerulein. 50 ug/kg of cerulein was administered. Two hours later, edema was induced by administration of LPS. 25 mg/kg of compound 18 was administered, and the changes of amylase and lipase, pancreatic digestive enzymes, were quantified.

FIG. 22 shows the levels of amylase and lipase, pancreatic digestive enzymes, in plasma. The model excessively increases digestive enzymes, which are released into blood. That is, the decrease of digestive enzyme in blood can be an indirect evidence for sample to reduce pancreatitis. As shown in FIG. 22, amylase and lipase were increased in the blood of the pancreatitis animal model, and the administration of 25 mg/kg of compound 18 significantly reduced the increase.

Figure 23:
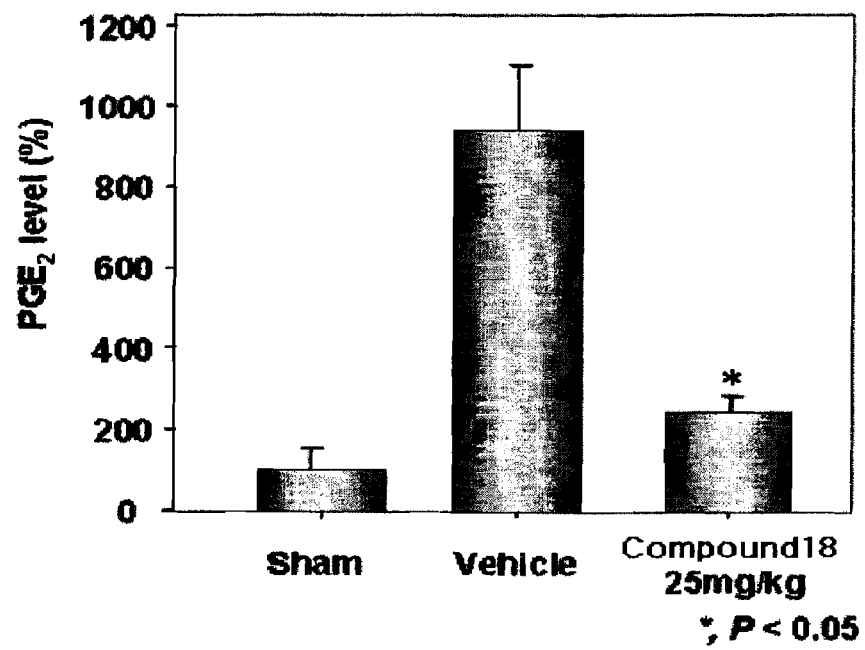
FIGS. 23 and 24 are efficacy test results using pancreatitis model induced by cerulein. The effects of the 2-hydroxybenzoic acid derivative of the present invention on TNF-α, IL-1β and PGE$_2$, inflammatory markers, were evaluated.
Figure 24:
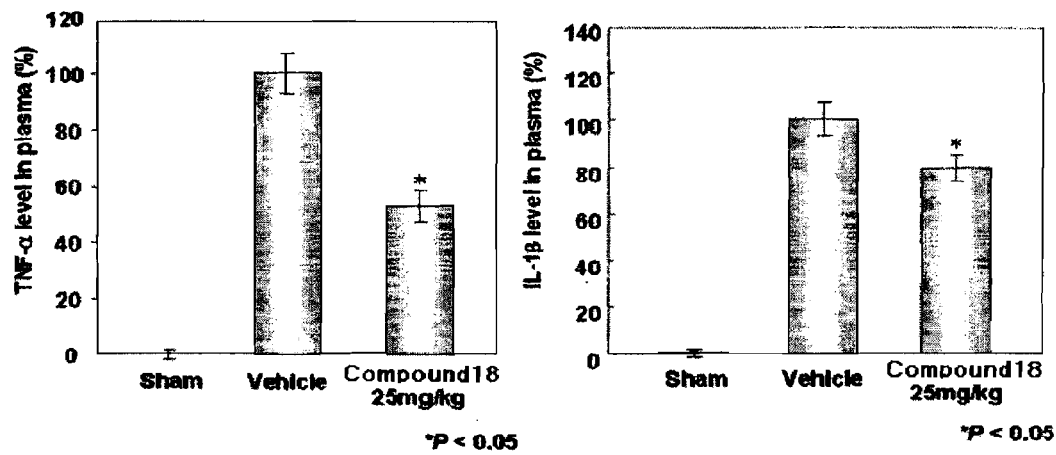

To confirm the protecting effect on inflammation, the levels of TNF-α and IL-10, inflammatory cytokines, were evaluated. $PGE_2$, the product of COX-2 (inflammation enzyme), were evaluated by ELISA method. TNF-α, IL-1β and $PGE_2$ were excessively increased in the pancreatitis model, and compound 18 significantly reduced these inflammation markers (FIGS. 23 and 24).

Example 9

Efficacy Test of Compound 2 in $APP_{swe}/PS1_{deltaE9}$ Double Transgenic Dementia Mice 9-1. Reduction Evaluation of Cytokines by ELISA Method APP/PS1 transgenic dementia mice were fed chow containing 25 mg/kg/day of compound 2 or 62.5 mg/kg/day of ibuprofen, for 7 months before being sacrificed (3.5~10.5 months). After administration of drug for 7 months, the levels of TNF-α, IL-1β and IL-6 were quantified by ELISA (mean±SEM, n=3-5). Significant difference from control (APP/PS1 mouse fed with general chow only), p<0.05 using one-way ANOVA according to Student-Neuman-Keuls' test.

Figure 25:
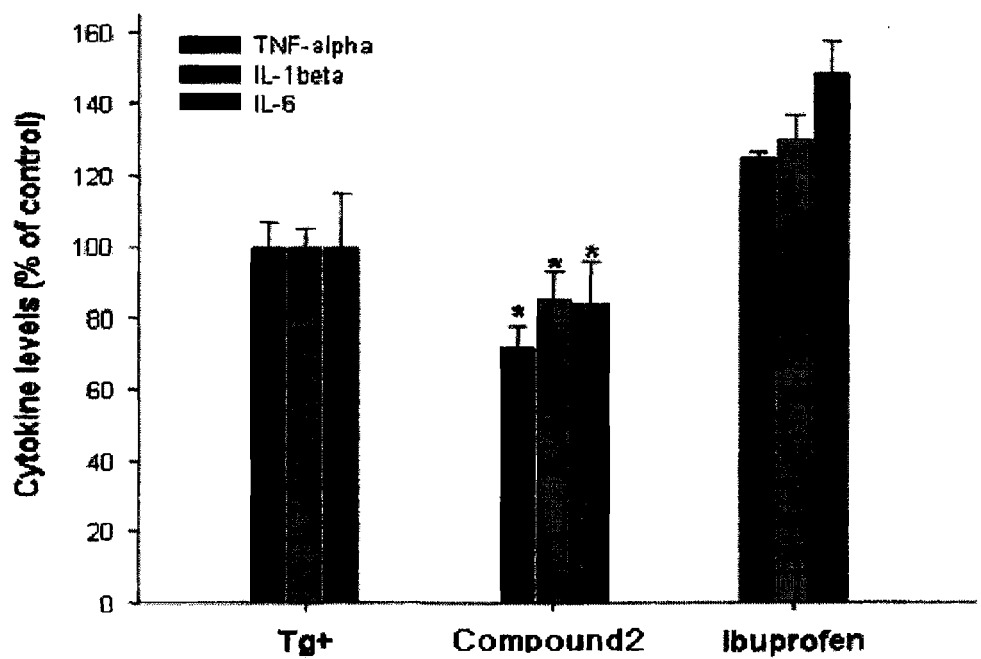
FIG. 25 are graphs showing the levels of TNF-α, IL-1β or IL-6 in brain of 10.5 month-old APP/PS1 dementia mouse (Tg+). The levels were evaluated by ELISA method. Compound 2 (25 mg/kg/day) or ibuprofen (62.5 mg/kg/day) mixed with chow was fed for 7 months from 3 month-old.

In result, treatment with compound 2 significantly reduced the levels of TNF-α, IL-β and IL-6 compared to APP/PS1 mouse fed with general chow only (FIG. 25).

9-2. Protecting Effect of Compound 2 on Brain-Blood Vessel Barrier

Figure 26:
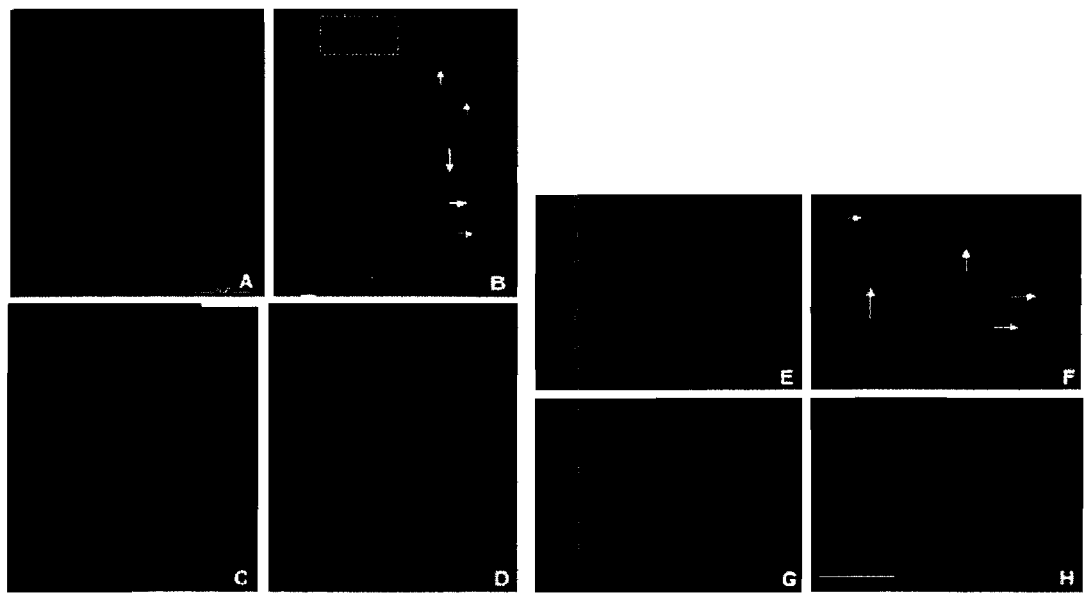
FIG. 26 is pictures (low and high magnification) showing protecting effect of compound 2 on brain-blood vessel barrier.
A: normal mouse
B/F: APP/PS1 dementia mouse
C/G: mouse administered compound 2 (25 mg/kg/day)
D/H: mouse administered ibuprofen (62.5 mg/kg/day)

Damage of brain blood vessel is well known in Alzheimer's disease. Protecting effects of compound 2 and ibuprofen (comparative example) on damage of brain-blood vessel barrier were evaluated. 3 ml/g of 2% Evans blue dye was administered into blood vessel of 5 month-old APP/PS1 dementia mouse. Chow containing 25 mg/kg/day of compound 2 or 62.5 mg/kg/day of ibuprofen was provided from 2 month-old to 5 month-old. In results, as shown in B and F of FIG. 26, the permeability of Evans blue dye was increased in cortex, hippocampus and thalamus, compared to normal mouse. In addition, as shown in FIG. 26, protecting effects on brain-blood vessel barrier were shown in group treated with compound 2 (C and G of FIG. 26) and group treated with ibuprofen (D and H of FIG. 26).

Figure 27:
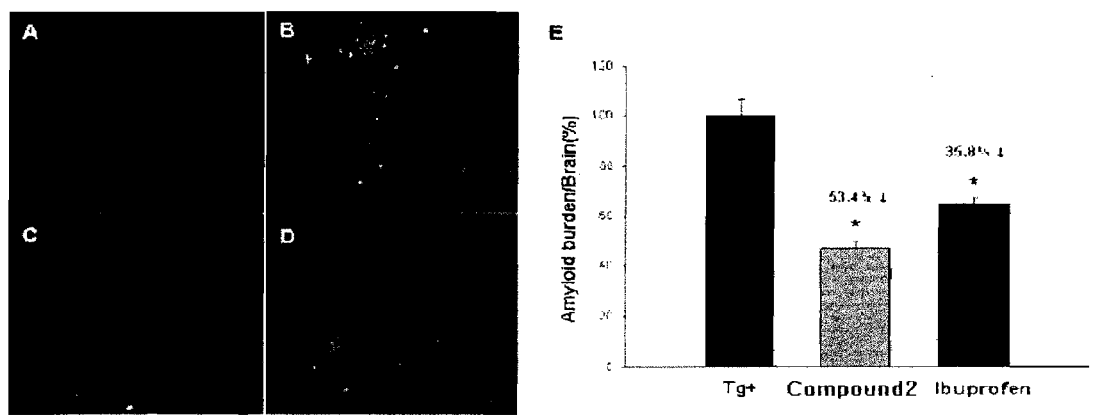
FIG. 27 is pictures of amyloid plaque produced in brain of 10.5 month-old normal mouse (A), 10.5 month-old APP/PS1 dementia mouse (B, Tg+), APP/PS1 dementia mouse fed with chow containing compound 2 (25 mg/kg/d, C) or ibuprofen (62.5 mg/kg/d, D), for 7 months from 3.5 month-old. Thioflavin-S pigment was used for staining. E is graphs quantifying results of A-D.

9-3. Reduction Evaluation of Compound 2 on Amyloid Plaque by Thioflavin-S Stain Analysis Effect of the 2-hydroxybenzoic acid derivative on dementia was evaluated with Thioflavin-S stain analysis. The treatment with 25 mg/kg/day of compound 2 for 7 months (from 3.5 to 10.5 month-old APP/PS1) caused a significant 53% reduction in amyloid plaque burden compared to APP/PS1 dementia mouse fed with general chow only (FIG. 27). In addition, the treatment with 25 mg/kg/day of compound 2 for 4 months (from 8.5 to 12.5 month-old APP/PS1) caused a significant 49.3% reduction in amyloid plaque burden compared to APP/PS1 dementia mouse fed with general chow only.

9-4. Behavior Improvement of Compound 2 by Elevated Plus Maze Test

APP/PS1 transgenic mice were fed chow alone or containing 25 mg/kg/day of compound 2, for 7 months (3.5~10.5 months). After administration of 7 months, Elevated plus maze test was performed to evaluate the behavior improvement. Elevated plus maze has two open arms (30 cm×6 cm×0.5 cm) and two closed arms (30 cm×6 cm×15 cm), and also has 6 cm×6 cm of center platform. In Elevated plus maze test, mouse was carefully laid in the center with the head of the mouse toward open arm. The time that the mouse spent in the open arm was recorded for 5 minutes (mean±SEM, n=3-5). *, Significant difference from control (APP/PS1 mouse fed with general chow only), p<0.05 using one-way ANOVA according to Student-Neuman-Keuls' test.

Figure 28:
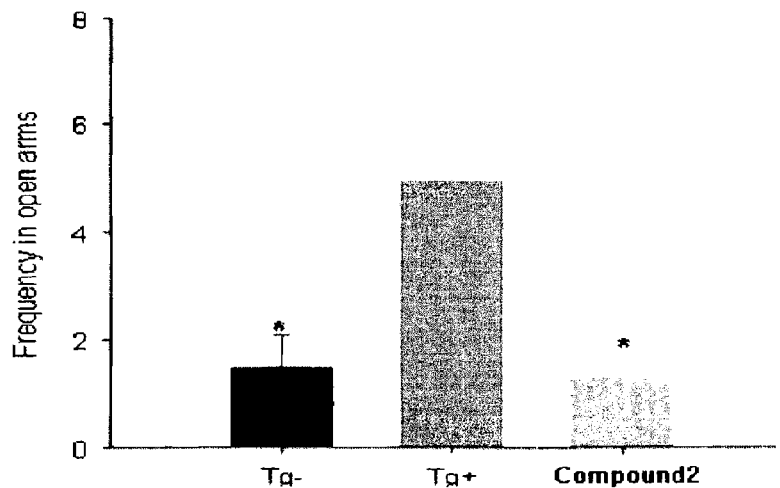
FIG. 28 is results of Elevated plus maze test performed with 10.5 month-old normal mouse, 10.5 month-old APP/PS1 dementia mouse, and APP/PS1 dementia mouse having administration of chow with compound 2 (25 mg/kg/d) for 7 months from 3.5 month-old. The time spent in the open arm was recorded as efficacy result.

In result, the group treated with 25 mg/kg/day of compound 2 for 7 months decreased the time for mouse to stay in the open arm compared to the group provided with chow only (FIG. 28).

Example 10

Efficacy Test of Compound 2 in G93A ALS Animal Model 10-1. Reduction of Microglia Activation G93A (Glycine ⇒ Alanine) transgenic mouse having similar pathophysiological characteristics with ALS (amyotrophic lateral sclerosis) human patient was used to evaluate therapeutic effect of drug in ALS, one of main degenerative brain diseases.

Figure 29:
FIG. 29 is pictures showing the activity of microglia, a marker of inflammation, in G93A mouse. The results were immunostained with TOMATO Lectin.
A: normal mouse
B: G93A mouse
C: G93A mouse administered 5 mg/kg/day of compound 2

Activation degree of microglia (a marker of inflammation in brain disease model) expressed in the lumbar ventral horn of G93A mouse were evaluated with TOMATO Lectin dye. In G93A mouse, microglia was more activated compared to the wild type mouse. In addition, treatment with 5 mg/kg/day of compound 2 decreased the number and activation degree of microglia (FIG. 29).

10-2. Reduction of Cytokine Expression

Figure 30:
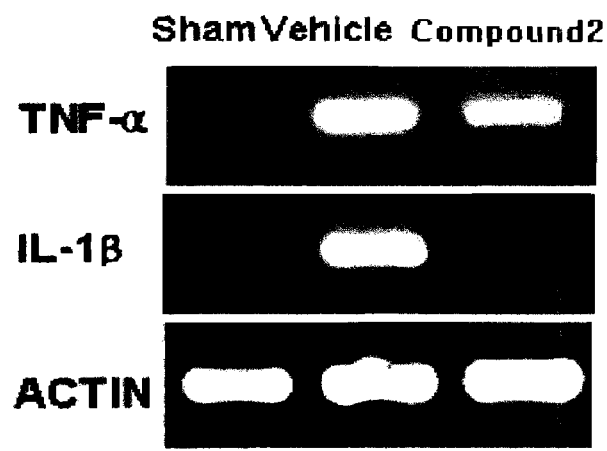
FIG. 30 is results showing the levels of mRNA of inflammatory cytokines (TNF-α and IL-1β), markers of inflammation, in G93A mouse. RT-PCR (Reverse Transcription-Polymerase Chain Reaction) was used.

Lumbar segments of 16 week-old G93A mice fed with general chow only, and 16 week-old G93A mice fed with chow containing 5 mg/kg/day of compound 2 were extracted and their RNA were separated. The mRNA expression degrees of TNF-α and IL-1β, inflammatory cytokines, were evaluated through RT-PCT. In results, administration of compound 2 effectively reduced inflammatory cytokines (FIG. 30).

Example 12

Efficacy Test of Compound 2 in Parkinson's Disease Animal Model

Figure 31:
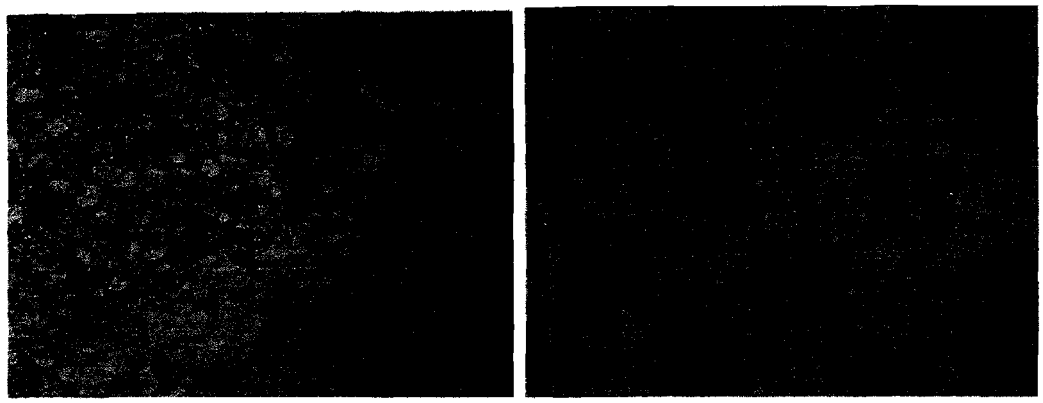
FIG. 31 is pictures showing suppressing effect of compound 2 on inflammation in Parkinson's disease animal model. The results were immunostained with CD11b.
A: mouse administered MPTP
B: mouse administered with 50 mg/kg/d of compound 2

MPTP (40 mg/kg) was subcutaneously injected into C57/BL6 mice (male/8 week-old). Some of the mice were administered with 50 mg/kg of compound 2 through intraperitoneal injection 30 minutes before the injection of MPTP everyday. Two days later, brain tissue was extracted and immunostained with CD11b. After reaction, DAB (diaminobenzidine) was used for chromograph, and then the activation degree of microglia (a marker of inflammation in brain disease model) was evaluated with optical microscope (FIG. 31).

In result, the activity of microglia caused by MPTP was decreased by the administration of compound 2.

The concrete diseases applicable with the compound or its pharmaceutically acceptable salt of the present invention are described as follows. However, the scope of the present invention is not limited to the diseases described below.

Application Example 1

Gastritis

The 2-hydroxybenzoic acid derivative of the present invention effectively suppressed cell death in experiments using cultured cell, induced by alcohol, *Helicobacter Pylori*, NSAID and $H_2O_2$. The compound of the present invention showed better effect than mucosta or PPI, known drugs having cell-protecting effect on gastritis. In addition, the compound of the present invention showed superior therapeutic effect on alcohol-induced gastritis in animal model, and alleviated gastritis induced by NSAID. The compound of the present invention also showed good safety in comparative experiment using aspirin because the compound did not any gastric bleeding even at much higher dose than that of aspirin. Therefore, the 2-hydroxybenzoic acid derivative of the present invention is thought to be useful for treating or preventing gastritis.

Application Example 2

Inflammatory Bowel Disease (IBD)

Prostaglandin (the product of cyclooxygenase (COX)) and leucotriene (the product of lipooxygenase) are known to take an important part in inflammation of inflammatory diseases like ulcerative colon. Zileuton, an inhibitor of 5-lipooxygenase (5-LOX), and sulfasalazine decreased the activity of MPO (myeloperoxidase) which is used as a marker showing the degree of inflammation in intestinal damage animal model (Singh V P et al., Indian J Exp Biol. 2004; 42(7):667-73). In addition, nimesulide (a selective COX-2 inhibitor) showed protective effect in two intestinal damage animal models (acetic acid-induced IBD and LTB4-induced IBD). Nimesulide excessively suppressed the activity of MPO in inflammation reaction (Singh V P et al., Prostaglandins Other Lipid Mediat. 2003; 71(3-4):163-75). Therefore, the compound of the present invention having anti-inflammatory effect can be effectively used for treating inflammatory bowel disease.

Application Example 3

Rheumarthritis

The 2-hydroxybenzoic acid derivative of the present invention showed similar or superior therapeutic effect in collagen-induced arthritis model compared to methotrexate (control), which is used for treating arthritis, but has adverse effects. In addition, the compound of the present invention alleviated pain of hyperalgesia induced by carrageenan and suppressed the production of inflammatory cytokines induced by zymosan. Therefore, the compound of the present invention having the similar efficacy with known anti-inflammatory agents and good safety can be used as therapeutic agent for arthritis.

Application Example 4

Pancreatitis

Acute pancreatitis is an inflammation related with pancreas autodigestion caused by reflux of digestive enzyme of pancreatic juice or bile of cholelithiasis into pancreas. Pancreatitis shows various symptoms like from mile edema to severe bleeding, which cause several damages to pancreas. There are a lot of evidences showing that pancreatitis is related with inflammation, and it is reported that COX inhibitor has a protective effect in pancreatitis model and suppresses the production of inflammatory markers, TNF-α and prostaglandin (Song A M et al., Am J Physiol Gastrointest Liver Physiol. 2002; 283(5):G1166-74). Therefore, the compound of the present invention can be effectively used for treating pancreatitis.

Application Example 5

Diabetic Inflammation and Pain

Roles of inflammation and pain are becoming important in type II diabetes. There are lots of literatures reporting that many drugs having anti-inflammatory effect reduce sign of type II diabetes or delay onset of type II diabetes (Deans K A et al., Diabetes Technol Ther. 2006; 8(1):18-27). Lisofylline, an anti-inflammatory compound, reduced diabetic symptoms 50% in mouse administered streptozotocin by suppressing IFN-gamma and TNF-alpha (Yang Z et al., Pancreas. 2003; 26(4):e99-104). Therefore, the compound of the present invention having anti-inflammatory effect can be effectively used for treating or preventing diabetic inflammation and pain.

Application Example 6

Arteriosclerosis

In early formation of atherosclerotic lesion of apolipoprotein E-deficient (apoE(−/−)) mouse, selective COX-2 inhibitor (for example, rofecoxib and NS-398) and non-selective COX inhibitor (for example, indomethacine) reduced atherosclerosis by about 35-38% and about 38-51%, respectively (Burleigh M E J Mol Cell Cardiol. 2005 September; 39(3): 443-52). Therefore, the compound of the present invention having anti-inflammatory effect can be effectively used for treating arteriosclerosis.

Application Example 7

Alzheimer's Disease

Alzheimer's disease is the most common form of adult onset dementia. Alzheimer's disease is characterized as the presence of the neurofibrillary tangles, amyloid plaques and severe neuronal death.

Also, there are lots of literatures showing that Alzheimer's disease is related with inflammation. It were often reported that microglia and inflammatory cytokines were increased in dementia animal model (Minghetti L. Current Opinion in Neurology 2005, 18:315-321), and that an administration of drug inhibiting inflammation may have a protecting effect in animal models of Alzheimer's disease (Townsend K P and Pratico D. FASEB J. 2005; 19(12): 1592-601).

Therefore, the compound of the present invention having cell-protecting effect and anti-inflammatory effect can be effectively used for treating Alzheimer's disease.

Application Example 8

ALS

Lou Gehrig Disease is named amyotrophic lateral sclerosis or motor neuron disease, and the progressive degeneration of motorneurones is the pathological hallmark of this disease.

There are lots of literatures showing that ALS is related with inflammation. It were often reported that microglia and inflammatory cytokines were increased in G93A mouse, animal model of ALS (Weydt P and Moller T. Neuroreport. 2005, 25; 16(6): 527-31), and an administration of drug inhibiting inflammation may have a protecting effect in animal models of ALS (West M et al., J Neurochem. 2004; 91(1): 133-43).

Therefore, the compound of the present invention can be effectively used for treating ALS.

Application Example 9

Parkinson's Disease

Parkinson's Disease (PD), the prototypic movement disorder, is characterized clinically by tremor, rigidity, bradykinesia and postural instability and diagnosed pathologically by a selective death of dopaminergic neurons in the substantia nigra.

There are lots of literatures showing that Parkinson's disease is related with inflammation. It were often reported that microglia and inflammatory cytokines were increased in Parkinson's disease (Gao H M, Trends Pharmacol Sci. 2003; 24(8): 395-401; Minghetti L. Curr Opin Neurol. 2005; 18(3): 315-21), and an administration of drug inhibiting inflammation may have a protecting effect in animal models of Parkinson's disease (Gao H M, Trends Pharmacol Sci. 2003; 24(8): 395-401).

Therefore, the compound of the present invention having cell-protecting effect and anti-inflammatory effect can be effectively used for treating Parkinson's disease.

INDUSTRIAL APPLICABILITY

The present invention provide a pharmaceutical composition useful for treating or preventing inflammatory disease, comprising the 2-hydroxybenzoic acid derivative represented by the chemical formula 1 or its pharmaceutically acceptable salt, and a method for treating or preventing inflammatory disease, using the pharmaceutical composition. The pharmaceutical composition of the present invention is very useful for treating or preventing inflammatory disease such as gastritis, pancreatitis, colitis, arthritis, diabetic inflammation, arteriosclerosis, nephritis, hepatitis, Alzheimer's disease, Parkinson's disease and Lou Gehrig's disease, as well as safe.

What is claimed is:

1. A method for manufacturing 2-acetoxy-5-[2-(4-trifluoromethyl-phenyl)-ethylamino]-benzoic acid at yield rate of at least 92%, comprising
   (S1) reacting 2-hydroxy-5-[2-(4-trifluoromethyl-phenyl)-ethylamino]-benzoic acid with di-tert-butyl dicarbonate;
   (S2) reacting 5-{tert-butoxycarbonyl[2-(4-trifluoromethyl-phenyl)-ethyl]amino}-2-hydrox-ybenzoic acid, which is made in the (S1) step, with acetyl halide; and
   (S3) removing tert-butoxycarbonyl group from 5-{tert-butoxycarbonyl[2-(4-trifluoromethyl-phenyl)-ethyl]amino}-2-acetox-ybenzoic acid, which is made in the (S2) step.

* * * * *